(12) United States Patent
Kakefuda et al.

US007083967B1

(10) Patent No.: US 7,083,967 B1
(45) Date of Patent: Aug. 1, 2006

(54) CYANOBACTERIAL NUCLEIC ACID FRAGMENTS ENCODING PROTEINS USEFUL FOR CONTROLLING PLANT TRAITS VIA NUCLEAR OR PLASTOME TRANSFORMATION

(75) Inventors: Genichi Kakefuda, Chapel Hill, NC (US); Hans Koop, Munich (DE); Stephen Sturner, Newton, PA (US); Rui-Guang Zhen, Morrisville, NC (US)

(73) Assignee: BASF Corporation, Research Triangle Park, NC (US)

( * ) Notice: Subject to any disclaimer, the term of this patent is extended or adjusted under 35 U.S.C. 154(b) by 770 days.

(21) Appl. No.: 09/893,033

(22) Filed: Jun. 27, 2001

Related U.S. Application Data

(60) Provisional application No. 60/214,705, filed on Jun. 27, 2000.

(51) Int. Cl.
 *C12N 9/88* (2006.01)
 *C12N 1/20* (2006.01)
 *C12N 15/00* (2006.01)
 *C07H 21/04* (2006.01)
 *A01H 1/00* (2006.01)

(52) U.S. Cl. ............... 435/232; 435/252.3; 435/320.1; 536/23.2; 530/350; 800/278; 800/300

(58) Field of Classification Search ............... 435/232, 435/252.3, 320.1; 536/23.2; 530/350; 800/278, 800/300
 See application file for complete search history.

(56) References Cited

U.S. PATENT DOCUMENTS

| 5,378,824 | A | 1/1995 | Bedbrook et al. | ......... 536/23.6 |
| 5,661,017 | A | 8/1997 | Dunahay et al. | ......... 435/172.3 |

FOREIGN PATENT DOCUMENTS

| JP | 6343473 | 12/1994 |
| WO | 96/28014 | 9/1996 |
| WO | 98/06862 | 2/1998 |
| WO | 98/20144 | 5/1998 |

OTHER PUBLICATIONS

Milano et al. [J. Gen. Microbiol. (1992), 138 : 1399-1408] See the attached sequence search alignment between Applicantions' SEQ ID NO: 6 and Accession No. M75906.*
Babczinski et al., 1995 Pestic. Biochem. Physiol.,52(1): 33-44 "Substituted Tetrahydropyrimidinones: A New Herbicidal Class of Compounds Inducing Chlorosis by Inhibition of Phytoene Desaturation".
Böger, P. and Sandmann, G., 1998 Pesticide Outlook, 6:29-35 "Carotenoid Biosynthesis Inhibitor Herbicides—Mode of Action and Resistance Mechanisms".

Chamovitz et al., 1993 J. Biol. Chem. 23: 17348-53. vol. 268 "Molecular and Biochemical Characterization of Herbicide-Resistant Mutants of Cyanobacteria Reveals that Phytoene Desaturation is a Rate-Limiting Step in Carotenoid Biosynthesis".
Clarke et al., 1985 Pestic. Biochem. Physiol., 23(3): 335-340 "Phytotoxicity of m-Phenoxybenzamides: Inhibition of Cell-Free Phytoene Desaturation".
Duggleby, 1997 Gene, 190: 245-249 "Identification of an Acetolactate Synthase Small Subunit Gene in Two Eukaryotes".
Dzelskalns & Bogorad, 1988 The EMBO Journal, vol. 7: 333-338 "Molecular Analysis of a Mutant Defective in Photosynthetic Oxygen Evolution and Isolation of a Complementing Clone by a Novel Screening Procedure".
Freidberg, D. et al., 1990 Z Naturforsch, C, 45(5): 538-543 "Molecular Characterization of Genes Coding for Wild-Type and Sulfonylurea-Resistant Acetolactate Synthase in the Cyanobacterium *Synechococcus* PCC7942".
Hattori et al., 1995 Mol. & Gen. Genet., 246: 419-425 "An Acetohydroxy Acid Synthase Mutant Reveals a Single Site Involved in Multiple Herbicide Resistance".
Kaneko et al., 1995 DNA Research 2:153-166 "Sequence Analysis of the Genome of the Unicellular Cyanobacterium *Synechocystis* sp. Strain PCC6803. I. Sequence Features in the 1 Mb Region from Map Positions 64% to 92% of the Genome".
Kowalczyk-Schroder & Sandmann, G., 1992 Pestic. Biochem. Physiol., 42(1): 7-12 "Interference of Fluridone with the Desaturation of Phytoene by Membranes of the Cyanobacterium *Aphanocapsa*".
Linden et al., 1990 Pesticide Biochem. Physiol., 36: 46-51 Biochemical Characterization of *Synechococcus* Mutants Selected against the Bleaching Herbicide Norflurazon.
Martinez-Ferez et al., 1992 Plant Molecular Biology 18: 981-983 "Nucleotide Sequence of the Phytoene Desaturase Gene from *Synechocystis* sp. PCCC 6803 and Characterization of a New Mutation which Confers Resistance to the Herbicide Norflurazon".

(Continued)

Primary Examiner—Tekchand Saidha

(57) ABSTRACT

This invention provides an alternative source of ahas and pds nucleic acids for plant transformation and selection. In particular, the invention provides ahas and pds nucleic acids from cyanobacteria, for example, *Synechocystis*, and expression elements of these genes for control of expression in plastids. The invention further provides nucleic acids encoding the acetolactate synthase (ahas) large subunit and the ahas small subunit which were found to provide herbicide resistance to plants. The present invention also provides a novel *Synechocystis* mutant phytoene desaturase (PDS) gene conferring resistance to 4'-fluoro-6-[(alpha, alpha, alpha,-trfluoro-m-tolyl)oxy]-picolinamide, a bleaching herbicide. The present invention provides improved methods involving cyanobacteria for the screening of compounds, including a new high throughput protocol that is a rapid and cost effective way to identify target site genes.

23 Claims, 15 Drawing Sheets

OTHER PUBLICATIONS

Figure 1A:
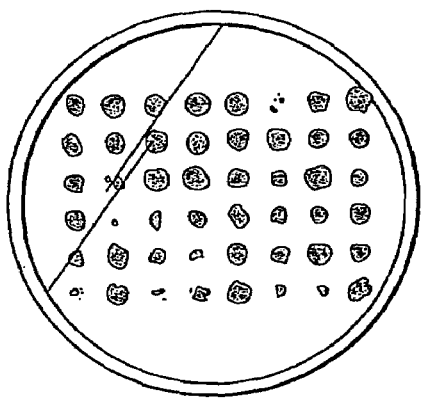

Martinez-Ferez et al., 1994 Pestic. Biochem. Physiol., 48: 185-190. "Mutagenesis of an Amino Acid Responsible in Phytoene Desaturase from *Synechocystis* for Binding of the Bleaching Herbicide Norflurazon".

Miflin, B.J., 1971 Arch Biochem. Biophys., 146: 542-550 "Cooperative Feedback Control of Barley Acetohydroxyacid Synthetase by Leucine, Isoleucine, and Valine".

Milano et al., 1992 J. Gen Microbiol 138: 1399-1408 "Molecular Characterization of the Genes Encoding Acetohydroxy Acid Synthase in the Cyanobacterium *Spirulina platensis*".

Porter, R.D., 1988 "[78] DNA Transformation," Methods in Enzymology, 167: 703-712.

Powell, et al., 1990 Br. Phycol. J., 25(1): 93 "Antibody probes to Investigate the Outer Surface of the Gas Vesicle".

Sandmann et al., 1991 Weed Science, 39: 474-479. "Phytoene Desaturase, the Essential Target for Bleaching Herbicides".

Sandmann et al., 1996 Z Naturforsch, 51(7-8): 534-538 "A New Non-Radioactive Assay of Phytoene Desaturase to Evaluate Bleaching Herbicides".

Sandmann & Fraser, 1993 Z Naturforsch, C, 48(3-4): 307-311 "Differential Inhibition of Phytoene Desaturases from Diverse Origins and Analysis of Resistant Cyanobacterial Mutants".

Sandmann et al., 1992 Res. Photosynth. Proc. Int. Congr., 3: 51-54. "Diversity of Phytoene Desaturating Enzymes and Corresponding Genes Involved in Carotenoid Biosynthesis of Photoautotrophic Prokaryotes".

Sandmann et al., 1992 Pestic. Biochem. Physiol., 42(1): 1-6 (1992) "Quantitative Structure-Activity Relationship of Fluridone Derivatives with Phytoene Desaturase".

Sandmann, 1993 Target Assays Mod. Herbic. Relat. Phytotoxic Compd., 15-20. "In Vitro Assay System for Phytoene Desaturase Inhibitors with Isolated Thylakoids".

Singh et al., 1988 Anal. Biochem., 171:173-179. (1988) "Assay of Acetohydroxyacid Synthase".

Singh et al., 1988 J. Chromatography, 444: 251-261 "Separation and Characterization of Two Forms of Aceto-Hydroxy Acid Synthase from Black Mexican Sweet Corn Cells".

Weinstock et al., 1992 J. Bacteriology., 174: 5560-5566 "Properties of Subcloned Subunits of Bacterial Acetohydroxy Acid Synthases".

Williams, 1988, Methods in Enzymology, 167: 766-778 "[85] Construction of Specific Mutations in Photosystem II Photosynthetic Reaction Center by Genetic Engineering Methods in *Synechocystis* 6803".

Windhöevel et al., 1994 Pestic. Biochem. Physiology, 49(1): 63-71 "Engineering Cyanobacterial Models Resistant to Bleaching Herbicides".

Windhöevel et al., 1997 Pestic. Biochem. Physiol., 57(1): 68-78 "Genetic Engineering of Resistance to Bleaching Herbicides Affecting Phytoene Desaturase and Lycopene Cyclase in Cyanobacterial Carotenogenesis".

Windhöevel et al., 1994 Plant Physiology, 104(1): 119-125 "Expression of Erwinia uredovora Phytoene Desaturase in *Synechococcus* PCC7942 Leading to Resistance against a Bleaching Herbicides".

* cited by examiner

CONCENTRATION OF
4'-FLOURO-6-[(ALPHA,ALPHA,ALPHA,
-TRIFLOURO-M-TOLYL)OXY]-
PICOLINAMIDE: 0

CONCENTRATION OF
4'-FLOURO-6-[(ALPHA,ALPHA,ALPHA,
-TRIFLOURO-M-TOLYL)OXY]-
PICOLINAMIDE: 2 μM

CONCENTRATION OF
4'-FLOURO-6-[(ALPHA,ALPHA,ALPHA,
-TRIFLOURO-M-TOLYL)OXY]-
PICOLINAMIDE: 5 μM

EXPERIMENT V, PLATE #1

EXPERIMENT VII, PLATE #2

EXPERIMENT VII, PLATE #3

EXPERIMENT VII, PLATE #4

WILD TYPE 5-1/12E 5-1/12F 7-2/1E 7-3/11F 7-3/12E 7-4/12F

Figures 1, 3:
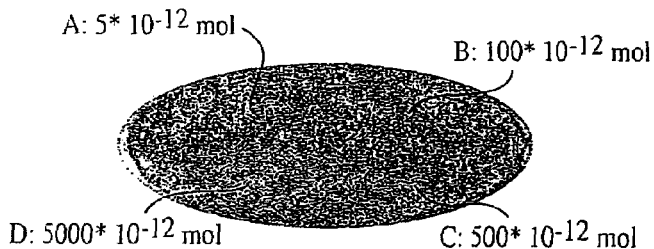
Figures 2, 3:
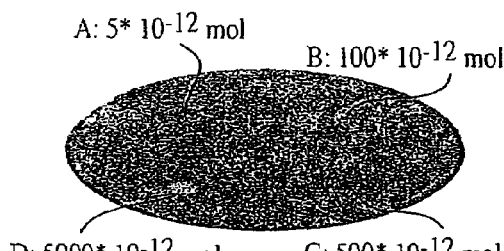
Figure 3:
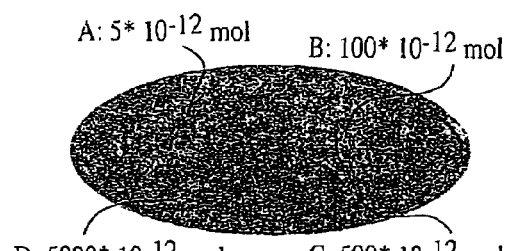
Figures 3, 4:
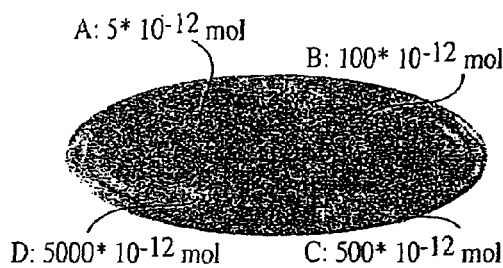
Figures 3, 4, 5:
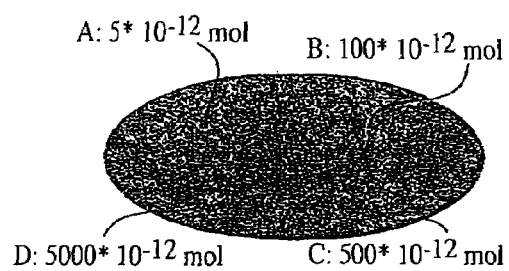
Figures 3, 4, 5, 6:
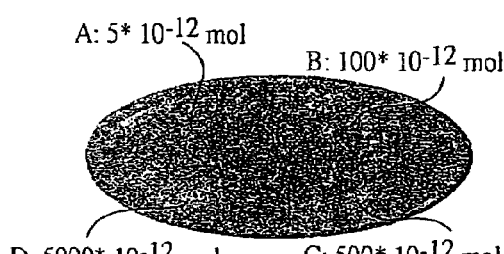

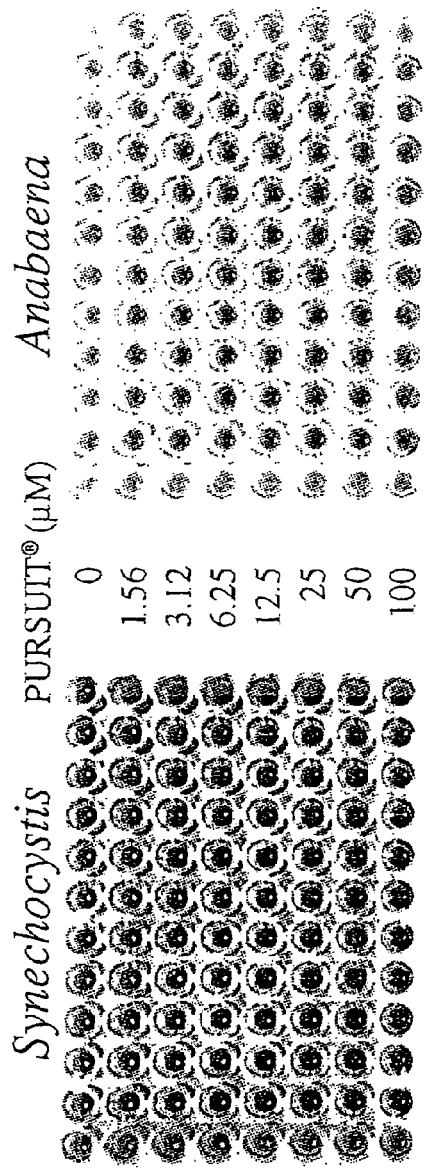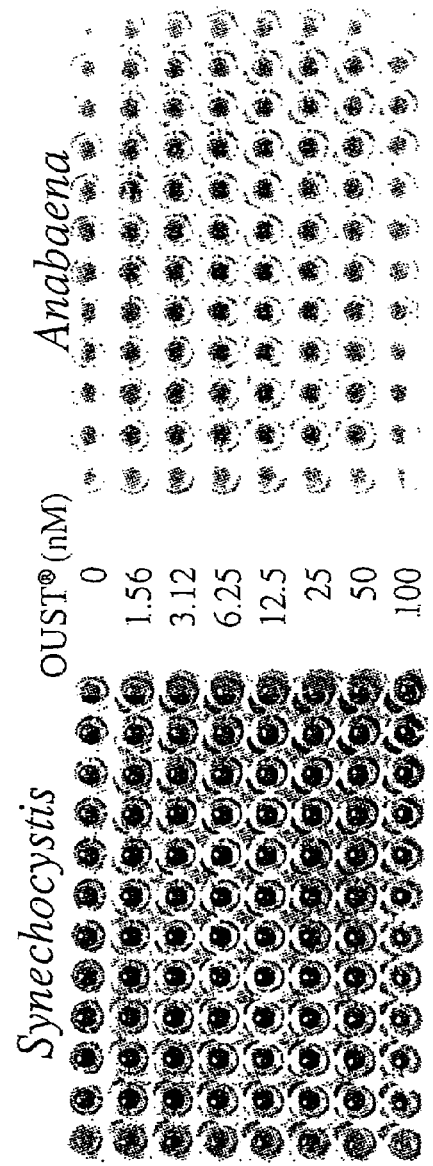
FIG. 6

FIGURE 11

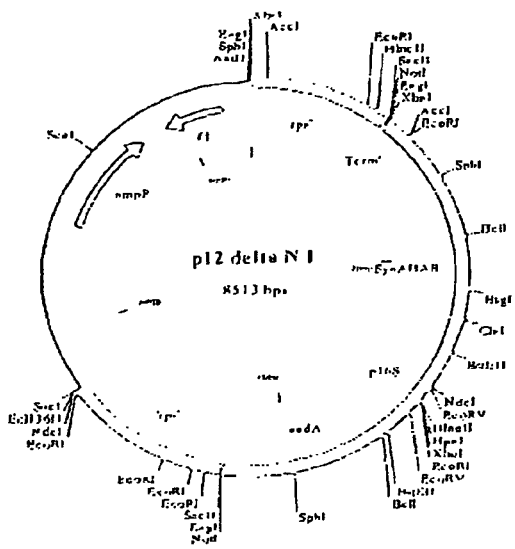

20 Oct 2000  
Page 1

Molecule Information

Molecule Definition:

Molecule:      p12 delta N 1.   8513 bps DNA Circular
File Name:     P12deli.cm5,  dated 25 Jun 1998

Description:   AHAS/aadA Cassette in p14 Delta N - orientation I

Notes:

Molecule Features:

| Type   | Start | End    | Name    | Description              |
|--------|-------|--------|---------|--------------------------|
| REGION | 7     | 927    | rps''   | chloroplast target sequence |
| REGION | 1115  | 962 C  | Term'   | Terminator               |
| REGION | 2954  | 1115 C | SynAHAS | Synechocystis AHAS       |
| REGION | 3069  | 2954 C | p16S    | Promoter                 |
| REGION | 3076  | 4460   | aadA    | aadA Cassette            |
| REGION | 4481  | 5561   | 'rps'   | chloroplast target sequence |
| GENE   | 6801  | 7661   | ampR    | Ampicillin Resistance Gene |
| GENE   | 8302  | 7347 C | f1      | f1 ori                   |

FIGURE 12

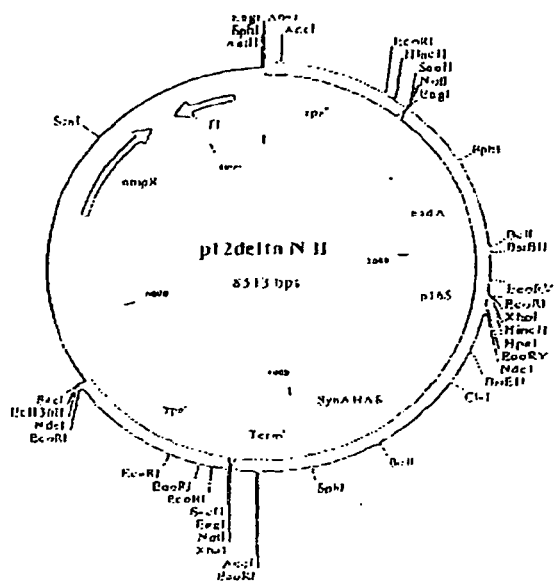

20 Oct 2000                    Molecule Information
Page 1

Molecule Definition:

Molecule:    p12delta N II, 8513 bps DNA Circular
File Name:   P12del11.cm5, dated 25 Jun 1998

Description: AHAS/aadA Cassette in p14 delta N Orientation II

Notes:

Molecule Features:

| Type   | Start | End  |   | Name   | Description               |
|--------|-------|------|---|--------|---------------------------|
| REGION | 7     | 927  |   | rps''  | chloroplast target sequence |
| REGION | 2332  | 948  | C | aadA   | aadA Cassette             |
| REGION | 2339  | 2454 |   | p16S   | Promoter                  |
| REGION | 2454  | 4293 |   | SynAHAS | Synechocystis AHAS       |
| REGION | 4293  | 4446 |   | Term'  | Terminator                |
| REGION | 4481  | 5561 |   | 'rps'  | chloroplast target sequence |
| GENE   | 6801  | 7661 |   | ampR   | Ampicillin Resistance Gene |
| GENE   | 8302  | 7847 | C | f1     | f1 ori                    |

FIGURE 15

SEQUENCE LISTING

<160> NUMBER OF SEQ ID NOS: 19

<210> SEQ ID NO 1
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 1
cgaattccct ggtagcattt aatacaaatt ggc                                    33

<210> SEQ ID NO 2
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 2
cgcataagct tgcagatgg agacggtttg ggc                                     33

<210> SEQ ID NO 3
<211> LENGTH: 1735
<212> TYPE: DNA
<213> ORGANISM: Synechocystis sp.

<400> SEQUENCE: 3

| | | |
|---|---|---|
| ccctggtagc atttaataca aattggctat cttggcaaag tcccccgaaa tattacgaaa | 60 |
| cgtaaagtat aataacaatc aacctgtaaa ccccaaatgc cttagcgaga cagtaaccca | 120 |
| tgcgcgttgt gatcgccgga gccggattag ccggcctagc ctgtgccaaa tacttagccg | 180 |
| atgcgggctt taccccgtc gtcttggaac gtagggatgt attaggcggg aagatcgccg | 240 |
| cgtggaaaga tgaggacgga gattggtacg aaaccggcct acacattttt tttggggcct | 300 |
| atcccaacat gttgcagtta tttaaggaat tggatatcga agatcgtctg caatggaaag | 360 |
| agcacagcat gatcttcaac caaccagaga aaccaggtac ctactctcgg ttcgattttc | 420 |
| cggatattcc ggccccatc aatggtttgg tagccattct tcgcaacaac gatatgctta | 480 |
| cctggccgga gaaaattcgc tttggcttgg gactcttgcc ggccattgtc cagggccaga | 540 |
| gctatgtgga agaaatggat aaatacactt ggtcagagtg gatggccaaa caaaatattc | 600 |
| cccccgcat cgaaaagaa gttttcattg ccatgagtaa gacgttgaac tttattgatc | 660 |
| ccgatgaaat ttccgccacc attttactta ctgccctcaa tcgcttttta caggaaaaaa | 720 |
| atggctctaa gatggcattc ctggatgggg caccaccgga gcgtctttgc caaccttttgg | 780 |
| tcgactatat tacggaacgg ggaggggaag tacacattaa taaacctctc aaagaaattt | 840 |
| tgcttaatga agatggttcc gttaagggtt acttaatccg gggcctagat ggagcccccg | 900 |
| acgaagtgat cacagcggat ttatatgtgt ctgccatgcc ggtggatccc ctgaaaacca | 960 |
| tggtgccagc gccctggaga gaatatcctg agtttaagca aatccaaggt ttggaaggag | 1020 |
| tcccggtcat taacctccac ctgtggtttg accgtaagtt aaccgacatt gatcatttgt | 1080 |
| tattctcccg atcgccgttg ttgagtgttt acgccgacat gagcaacacc tgccgagaat | 1140 |
| acagtgatcc agacaaatcc atgttggaat tggtgctggc tccggcccag gattggatcg | 1200 |
| gcaaatccga cgaagagatt gtggcggcca ccatggcgga gatcaagcaa ctctttcccc | 1260 |
| aacacttcaa cggggataat ccagcccgac tgcttaaatc ccacgtggtc aaaaccccc | 1320 |

```
gctcagtcta caaagctacc cccggaaggc aggcttgtcg ccccgatcaa cggacatcgg      1380
tgcccaactt ttacctagca ggggacttca ccatgcaaaa atacttgggc agtatggaag      1440
gggcggtgct ttccggcaaa caatgcgccc aggcgatcgc cgccgatttc aaccccccaaa     1500 ccgttccccc caccagggaa atagtcaccg tgggttaagc cgcctggact ccctggtaat      1560
cttcctgaca aatggcaacc ctaatgcgac aatgctaaat ggctaacggt caaatttctc      1620
cccagcgtgc agttaccaaa ccccaatcct ggtggctgac ttccgaaccc cgtccgtcct      1680
taatgttaca actgcccaaa ccgtctccat ctgcaaagcc ctgtgcttct gttga           1735
```

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (3)
<223> OTHER INFORMATION: a, g, c or t
<220> FEATURE:
<221> NAME/KEY: modified_base
<222> LOCATION: (6)
<223> OTHER INFORMATION: a, g, c or t
<220> FEATURE:
<221> NAME/KEY: modified_base
<222> LOCATION: (12)
<223> OTHER INFORMATION: a, g, c or t

<400> SEQUENCE: 4

```
ggnacngayg cnttycarga                                                  20
```

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (10)
<223> OTHER INFORMATION: a, g, c or t
<220> FEATURE:
<221> NAME/KEY: modified_base
<222> LOCATION: (13)
<223> OTHER INFORMATION: a, g, c or t

<400> SEQUENCE: 5

```
ytsccaytgn cknaccat                                                    18
```

<210> SEQ ID NO 6
<211> LENGTH: 1959
<212> TYPE: DNA
<213> ORGANISM: Synechocystis sp.
<220> FEATURE:
<221> NAME/KEY: modified_base
<222> LOCATION: (1843)
<223> OTHER INFORMATION: a, t, c, g, other or unknown

<400> SEQUENCE: 6

```
gccataggag cccatcgccg attgagttca aattagaagc acttagccta cgcttcctaa      60
accgattgtc cagtggttgc atcaattcct aatcccaaaa caaatttcct gaaaactgtt     120
cctagccaac ggcaaaccgg ggcttatatc ctgatggata gcctgaaacg ccatggggtc     180
aaacacattt ttggctatcc cggcggggca attttgccca tctatgatga actgtaccgc     240
```

-continued

```
tttgaagcgg cgggggaaat tgagcatatt ttggtgcgcc atgaacaagg agcttcccat    300
gcggcggatg ggtatgccag agccacaggt aaagtgggag tttgtttcgg tacatctgga    360
ccaggggcga ctaacttggt gaccggcatt gccaatgccc atttggactc ggtgcccatg    420
gtggtgatta ctgagagggt gggccgtgcc atgattggta gcgatgcttt ccaggaaatt    480 gacattttg gcatcacctt accgatcgtt aagcactcct atgtggtacg tagtgcggcg    540
gatatggctc gcattgttac tgaggctttc catcttgcta gcaccggtcg tcccgggccg    600
gttttgatcg atattcccaa ggatgtgggc ttagaagaat gtgagtacat tcccctcgac    660
cccggtgacg ttaatctacc gggttatcgc cccacggtta aggtaatcc ccgacaaatt    720 aatgcggcat tgcaattgtt ggagcaggcc agaaatccct tgctctacgt aggggaggg    780 gcgatcgccg ccaatgccca tgcccaggtg caggaatttg cggaaaggtt ccagttgccg    840
gtaacaacca ccctgatggg aattgggct tttgacgaaa accatcccct ttcggtgggt    900
atgttgggta tgcatggcca ccgctatgcc aactttgccg tcagcgaatg tgatttgttg    960
attgcagtgg gggcccgttt cgacgaccgg gtaactggca aactagacga atttgctagc   1020
cgcgccaaag taattcacat tgacatcgac cggcgagg tgggaaaaaa cagggctccc     1080
gatgtgccca ttgtggggga tgtacgccat gttttagaac agcttttgca gcgggcccgg    1140
gaattggatt accccaccca tccccatacc acccaggcat ggttaaatcg cattgatcat   1200
tggcggaccg attaccccct ccaggtgccc cactatgagg atactattgc cccccaggag    1260
gtagtacacg aaattggtcg ccaggccccc gatgcctact acaccaccga tgtgggacaa   1320
caccaaatgt gggcggccca gttttttgaac aatggccccc gccgatggat ttccagtgct   1380
ggcttgggta cgatgggctt tggtttacct gccgccatgg gagccaaagt gggagtgggg    1440
gacgagcggt catttgcatc agtggagatg ccagcttcca aatgaatctt caggaactgg    1500
gaaccctagc ccagtacgac atccaggtta aaactattat tctcaataac ggttggcagg    1560
ggatggtgcg tcagtggcaa caaactttct acgaagaacg ttattctgct tctaacatgt   1620
cccagggcat gccagacatt aatctcctct gtgaagccta tggcatcaag ggtattactg    1680
tgcgcaagcg ggaagatttg gccccggcga tcgccgaaat gctagcccac aatggtcctg    1740
tggtgatgga tgtggtggtc aaaaaagatg aaaactgtta ccctatgatt gcccccggca   1800
tgagtaatgc ccaaatgcta ggtttaccgg aagtgccggt acnggacaat ggtccccgga    1860
tggtggagtg caaccattgc caaacccaaa atttcatcac ccatcgtttc tgttctggtt    1920
gtggagccaa actctaaccc ataagccaaa attgaattc                          1959
```

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 7
attgacattt ttggcatc                                                    18

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 8

-continued tatccgccgc actacgtac                                        19

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 9 cagggcgac taacttggtg ac                                     22

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 10
accgctatgc caactttgcc gt                                    22

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 11
ggaggatagt acacgaaatt gg                                    22

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 12
aaatcttccc gcttgcgcac ag                                    22

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 13
ccaatttcgt gtactacctc ctg                                   23

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 14
aaagtgggag tggggacga a                                      21

<210> SEQ ID NO 15
<211> LENGTH: 22
<212> TYPE: DNA

-continued

```
<213> ORGANISM: Artificial Sequence
<220> FEATURE:
<223> OTHER INFORMATION: Description of Artificial Sequence: Primer

<400> SEQUENCE: 15
cggtggaatt taccccaat gg                                              22

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 16
ggccctaaaa cttggattcc agg                                            23

<210> SEQ ID NO 17
<211> LENGTH: 565
<212> TYPE: DNA
<213> ORGANISM: Synechocystis sp.

<400> SEQUENCE: 17
gtggaatttt accccaatgg ccaccggcga tcgccttctt tgcccccat gaaacacacc      60 ctctctgttt tagttgaaga tgaagccgga gtgctaaccc gcattgccgg actatttgcc    120
cgccgtggtt ttaacattga gacttggcg gtggggtcgg cggaacaggg ggacgtttcc    180
cgcatcacca tggtggtgcc gggggatgag aacaccatcg aacaactgac caagcaactc    240
tacaagttgg ttaacgtaat taaagtacag gacatcaccg aaactccctg tgtggaaagg    300
gaattgatgc tggtgaaggt gagcgccaat gcccctaacc gagcggaagt gattgagcta    360
gcccaggtat tccgggcccg cattgtggat atctccgaag acaccgtcac catcgaatgg    420
tgggggaccc gggtaaaatg gtagcaatcc tccagatgtt ggccaagttg gcattaaaga    480
ggtggctcga acgggcaaaa ttgctttggt gcgggaatcc ggcgtcaata cggaatatct    540
gaaatccctg gaatccaagt tttag                                         565

<210> SEQ ID NO 18
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 18
ggctgatatc ctgatggata gcctg                                          25

<210> SEQ ID NO 19
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 19
ttggcttacc ggttagagtt tggctccaca                                     30
```

CYANOBACTERIAL NUCLEIC ACID FRAGMENTS ENCODING PROTEINS USEFUL FOR CONTROLLING PLANT TRAITS VIA NUCLEAR OR PLASTOME TRANSFORMATION

CROSS REFERENCE TO RELATED APPLICATIONS

This application claims priority to U.S. Provisional Patent Application Ser. No. 60/214,705, filed Jun. 27, 2000, the entire contents of which are hereby incorporated by reference.

FIELD OF THE INVENTION

The present invention relates to improved screening methods for identifying and utilizing cyanobacterial genes for modifying plant traits, and to cyanobacteria as an alternative source of ahas and pds genes for plant transformations, in particular genes encoding herbicide insensitive proteins, and elements of genes for control of expression in plastids.

BACKGROUND OF THE INVENTION

Cyanobacteria are considered to be the precursor of plant chloroplasts. Cyanobacteria possess all beneficial features of prokaryotes like ease of handling, rapid growth under defined conditions, availability of replica plating techniques, easy genetic manipulation by mutagenesis or transformation and availability of established mutants. Cyanobacterial metabolism also share important features with higher plant metabolism such as oxygenic photosynthesis by two photosystems and autotrophy with respect to reduced nitrogen, sulfur and carbon dioxide. Therefore, efficacy of compounds in cyanobacteria can be indicative of similar performance in higher plants.

The photosynthetic membranes of cyanobacteria, plants and algae contain essential pigments called carotenoids, which function in protecting chlorophyll against photo oxidative damage by singlet oxygen, as well as acting as accessory pigments in photosynthetic light harvesting. These carotenoids are also precursors of vitamin A in human and abscissic acid in plants. The first committed step in carotenoids biosynthesis is the condensation of two molecules of geranylgeranyl pyrophosphate (GGPP) to yield the colorless phytoene. Desaturation of phytoene through the insertion of four double bonds gives rise to lycopene, and further cyclization reactions lead to the generation of β-carotene. Phytoene desaturase(pds) mediates the first two steps of desaturation of phytoene, disruption of which results in an observable bleaching symptom. As such, a number of commercial herbicides directed at inhibiting this enzyme have been developed, e.g. norflurazon, fluridone, and fluorochloridone.

In addition, as ancestral precursors to chloroplasts, cyanobacterial genes share features common to chloroplast genes. Gene elements, such as promoters, ribosome binding sites, etc. are similar and can be cross-functional between chloroplast and cyanobacteria. Therefore cyanobacterial genes make ideal candidates for plastome targeted transformation, and in particular chloroplast transformation.

There are a number of references in the literature to screening methods and assays utilizing cyanobacteria. These include methods using cyanobacteria for the screening of compounds to identify inhibitors of specific metabolic pathways and identification of novel herbicidal modes of action. [Hirschberg et al, 1996] describes an *Erwinia* gene transformed into host cells selected of cyanobacteria, specifically *Synechococcus* PCC 7942 and *Synechocystis* PCC 6803, which was used as a screen for beta-carotene biosynthesis and for mutants resistant to herbicides specifically bleaching herbicides of the trialkylamine family. The screening for bleaching activity is described by [Sandmann et al, 1991] as a means to discover new herbicides with different core structures which inhibit phytoene desaturase (pds), a membrane bound enzyme in the carotenogenic pathway catalyzing the hydrogen abstraction step at the first C40 precursor of beta-carotene. [Windhoevel et al, 1994] describes a screen involving genes coding for pds of the non-photosynthetic bacterium *Erwinia uredovora* introduced into the cyanobacterium *Synechococcus* as a convenient experimental model for higher plant transformation and resistance to herbicides. The functionality of the heterologously expressed phytoene desaturase in the transformants was demonstrated in assays. Other references such as [Babczinski et al, 1995] identify new herbicide class inhibiting pds based on a screen utilizing the unicellular cyanobacteria *Anacystis*. [Chamowitz et al, 1993] described a cell-free carotegenic assay to identify herbicide resistant algal pds mutants. Inhibition of carotenoid biosynthesis by herbicidal m-phenoxybenzamide derivatives was investigated in a cell-free in vitro assay using the cyanobacteria *Aphanocapsa* by [Clarke et al, 1985], and subsequently by [Kowalczyk-Schroeder et al, 1992]. [Sandmann et al, 1991], describes a non-radioactive cell-free assay to quantitatively determine inhibition of plant-type pds by bleaching herbicides. They further developed a cyanobacterial pds assay system, a mode of action assay utilizing the cyanobacteria *Anacystis*, and assays using algal cells. The present invention, however, differs by identifying improvements to the current screening methods and assays, and uses these improvements to identify novel nucleic acid fragments having herbicide resistance mutations in the pds gene.

The prokaryotic acetolactate synthase (ahas) enzyme exists as two distinct, but physically associated, protein subunits. In prokaryotes, the two polypeptides, a "large subunit" and a "small subunit" are expressed from separate genes. Three major ahas enzymes, designated I, II, III, all having large and small subunits have been identified in enteric bacteria. In prokaryotes, the ahas enzyme has been shown to be a regulatory enzyme in the branched amino acid biosynthetic pathway [Miflin et al, 1971], and only the large subunit has been observed as having catalytic activity. From studies of ahas enzymes from microbial systems, two roles have been described for the small subunit: 1) the small subunit is involved in the allosteric feedback inhibition of the catalytic large subunit when in the presence of isoleucine, leucine or valine or combinations thereof, and 2) the small subunit enhances the activity of the large subunit in the absence of isoleucine, leucine or valine. The small subunit has also been shown to increase the stability of the active conformation of the large subunit. The expression of the small subunit can also increase the expression of the large subunit as seen for AHAS I from *E. coli* [Weinstock et al., 1992].

The ahas large subunit protein has been identified in plants, and has also been isolated and used to transform plants. An ahas mutant allele isotype of the ahas III large subunit protein, having the tryptophan at position 557 replaced with leucine has been found in a *Brassica napus* cell line [Hattori et al., 1995]. The mutant protein product of this gene confers sulfonylurea, imidazolinone and triazolopyridine resistance to the cell line. This mutant allele, when expressed in transgenic plants, also confers resistance to these herbicides.

Until recently, there was no direct evidence that a small subunit protein of ahas exisited in eukaryotic organisms. Recently, other groups, through the use of Expressed Sequence Tags (ESTs), have identified sequences homologous to the microbial ahas small subunit genes in an eukaryote, the plant *Arabidopsis*. These groups showed that a randomly isolated *Arabidopsis* cDNA sequence had sequence homology with the ahas small subunit sequences from microbial systems. Since then, ESTs from small subunit genes have been described from other eukaryotes such as yeast and red algae. [Duggleby et al, 1997] describes three EST sequences, two from *Arabidopsis* and one from rice, that have homology to known prokaryotic small subunit cDNA sequence from *P. purpurea*.

Several references to ahas screens and assays utilizing cyanobacteria exist in the prior art. [Powell et al, 1990], reported on the role of cyanobacteria for herbicide screening but no mention was made of the ahas "small subunit" identified in our invention. They reported that our understanding of the mode of action of certain herbicides which inhibit photosynthesis has been facilitated by studies with cyanobacteria. In the case of sulfonylurea herbicides which inhibit branched chain amino acid biosynthesis, the resistance shown by a cyanobacterium is due to an insensitive acetolactate synthase enzyme. These studies are not consistent with the results reported by Freiburg et al. discussed below, in which the cyanobacterial gene is sensitive. If other insensitive target enzymes were to be found, cyanobacteria could be useful sources of genes for the cloning of herbicide resistance into higher plants. They presented data showing high levels of resistance of certain cyanobacteria to glyphosate, an inhibitor of aromatic amino acid biosythesis. [Dunahay et al, 1997], discloses a method to transform chlorophyll containing algae, which includes introducing a recombinant molecule comprising a nucleic acid molecule encoding a dominant selectable marker operatively linked to an algal regulatory control sequence into the chlorophyll C-containing algae. However, unlike our invention, the mutant ahas was introduced into algae, not cyanophycae, to detect inhibitors.

WO 98/06862 (Calgene) discloses plants transformed with the *Erwinia* phytoene desaturase gene for altered carotenoid levels and fatty acid. JP 6,343,476 (Kirin Brewery) describes the production of bleaching herbicide-resistant plants by transformation with the *Erwinia* pds gene. WO 98/06862 (Zeneca) discloses transgenic plants resistant to many classes of herbicides but the source of the genes, whether pds or ahas or from *Synechocystis* is unspecified. Also, U.S. Pat. No. 5,378,824 (Dupont) and U.S. Pat. No. 5,661,017 (Dunahay et al.) both report the transformation of a plant ahas gene, not a *Synechocystis* gene, into a number of phyla and classes including algae.

Freiburg et al, 1990, reported on herbicide resistant *Synechococcus* ahas gene expressed in *E. coli*. The report describes the isolation and molecular characterization of acetolactate synthase genes from the sulfonylurea-sensitive enzyme and from the sulfonylurea-resistant mutant, which specifies the enzyme resistant to sulfonylurea herbicides. The ALS gene was cloned and mapped by complementation of an *E. coli* ilv auxotroph that requires branched-chain amino acids for growth and lacks ALS activity. The cyanobacterial gene is efficiently expressed in this heterologous host. The resistant phenotype is a consequence of proline to serine substitution in residue 114 of the deduced amino acid sequence. Functional expression of the mutant gene in *Synechococcus* and in *E. coli* confirmed that this amino acid sequence is responsible for the resistance. [Linden et al, 1990], reported cyanobacteria *Synechococcus* PCC 7942 mutants selected against the bleaching herbicide norflurazon. One strain exhibited cross-resistance against another bleaching herbicide fluorochloridone, but the other three strains did not show cross-resistance against other phytoene desaturase (pds) inhibitors. [Sandman et al, 1991] reported on mutants from *Synechococcus* PCC 7942, which were selected for tolerance to various bleaching herbicides. A mutant NFZ4 established a high degree of cross-resistance to both norflurazon and fluorochloridone, but not to fluridone. [Chamowitz et al, 1991] cloned and sequenced a pds gene from the cyanobacteria *Synechococcus* PCC 7942, also resistant to the bleaching herbicide norflurazon. The identified mutant is a Val⇒Gly change at position 403 in the *Synechococcus* but not *Synechocystis* pds protein. [Sandmann et al, 1998] reported bacterial and fungal pds as a target for bleaching herbicides, and discussed the identification of cyanobacterial mutants with resistance to specific compounds and their cross-resistance to other bleaching herbicides.

Cyanobacteria *Synechocystis* was originally described in Vioque et al, 1992. A spontaneous mutant, strain AV4, which is resistant to norflurazon, was isolated from *Synechocystis* PC 6803. DNA isolated from the mutant AV4 can transform wild-type cells to norflurazon resistance with high frequency. Sequence analysis of the clone identified an open reading frame that is highly homologous to the previously sequenced pds genes from *Synechococcus* and soybean. In both cyanobacteria and plants the pds gene is highly conserved: the *Synechocystis* PCC 6803 pds gene is 82% and 61% identical to the *Synechococcus* PCC 7942 and the soybean pds genes respectively. [Sandmann et al, 1994] identified three distinct *Synechocystis* mutants selected against norflurazon, and showed modification of the same amino-acid of phytoene desaturase into three different ones. In all cases, the same amino-acid $Arg^{195}$ was modified either into Cys, Pro or Ser. The degree of resistance was highest when Arg was changed into Ser.

While the literature has several references to pds herbicide resistant transgenic plants, our intervention exemplifies improvements to current cyanobacteria screening methods. Our improvement has identified novel nucleic acid fragments from *Synechocystis* PCC 6803. The mutant pds (phytoene desaturase) gene and ahas large and small subunits are useful in the identification of novel pds and ahas inhibitors and, in plant transformations for conferring resistance and cross-resistance to certain bleaching herbicides and AHAS-inhibiting herbicides.

SUMMARY OF THE INVENTION

Therefore, the present invention improves the current cyanobacteria screening methods. Our improvement has, in turn, identified novel nucleic acid fragments from the cyanobacterial *Synechocystis* PCC 6803. The mutant pds (phytoene desaturase) gene and ahas (Acetohydroxyacid synthase) large and small subunits are useful in the identification of novel pds and ahas inhibitors and, in plant transformations for conferring resistance and cross-resistance to certain bleaching herbicides and imidazolinones.

Specifically, screening methods were used for identification of novel *Synechocystis* mutations that provide resistance to 4'fluoro-6-[(alpha,alpha,alpha,-trifluoro-m-tolyl)oxy]-picolinamide, an inhibitor of pds.

The identification of a novel mutation in the pds gene together with the fact that this gene is highly homologous between cyanobacteria and plants, will aid our efforts in engineering crops for resistance to herbicides through the introduction of site-directed mutation in the target pds gene.

Figure 13:
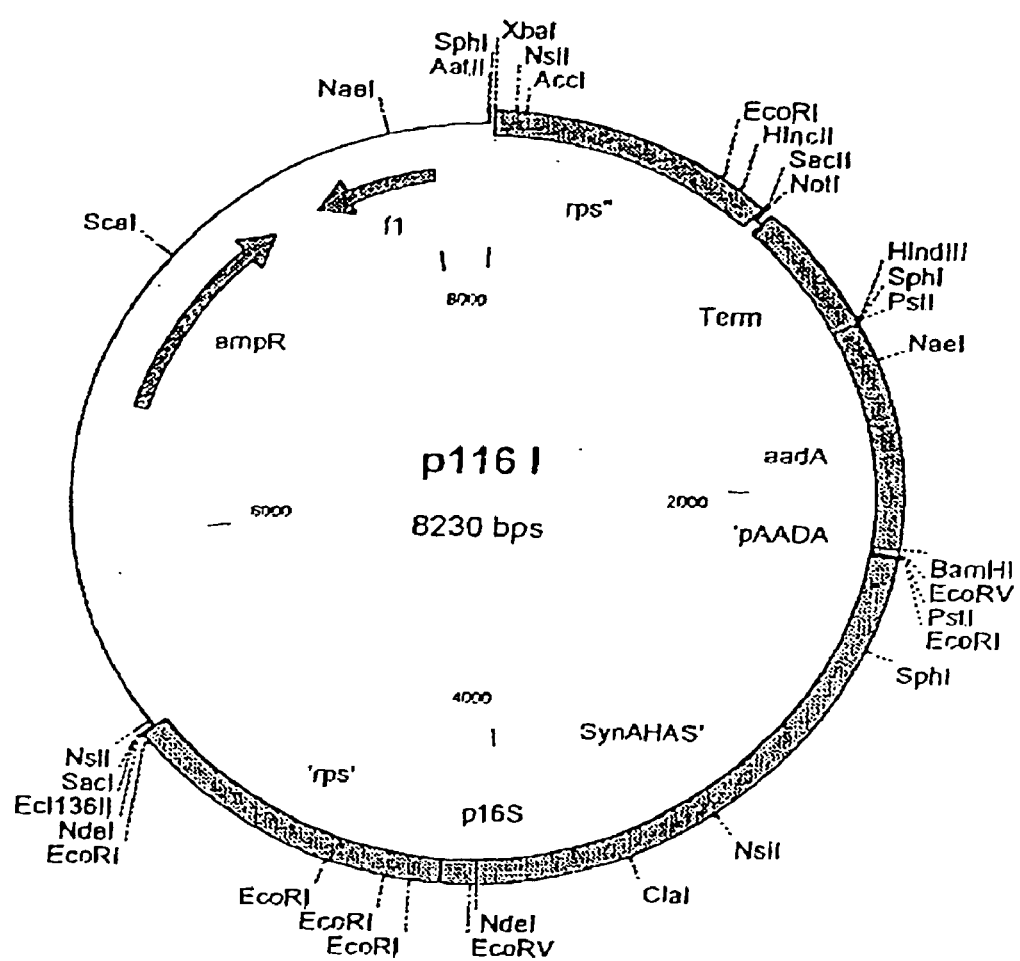
Figure 14:
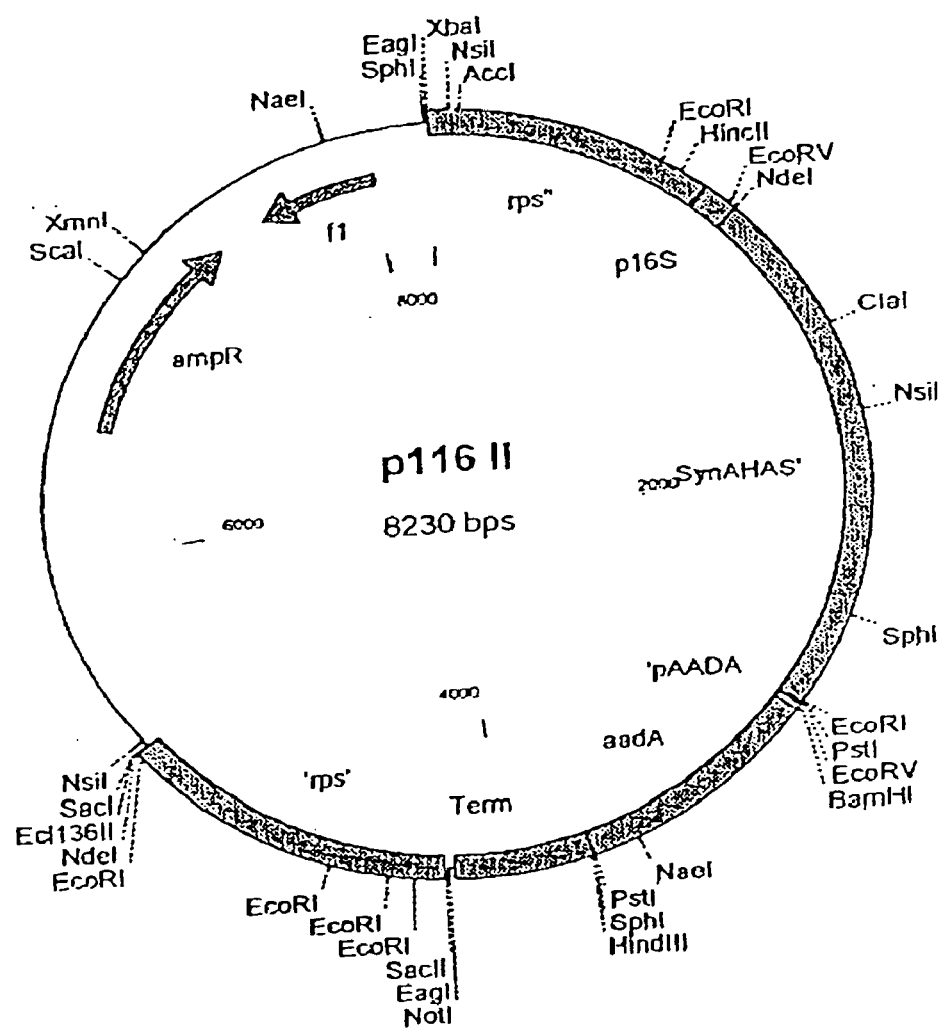

Novel mutations displaying unique resistance to 4'-fluoro-6[(alpha,alpha,alpha,-trifluoro-m-tolyl)oxy]-picolinamide will aid in programs of engineering crops for resistance to 4'-fluoro-6-[(alpha,alpha,alpha,-trifluoro-mtolyl)oxy]-picolinamide and potentially other pds inhibiting herbicides via chloroplast-mediated transformation. Alternatively, mutant forms of pds genes with mutation(s) at position(s) similar to the *Synechocystis* gene can be obtained for any given crop species, and used further for genetic transformation. The identification of additional novel mutations conferring resistance to 4'-fluoro-6-[(alpha,alpha,alpha,-trifluoro-m-tolyl)oxy]-picolinamide should shed light on the structure of 4'-fluoro-6[(alpha,alpha,alpha,trifluoro-m-tolyl)oxy]-picolinamide binding site, and serve as a valuable guide for designing novel inhibitors of this enzyme.

Therefore, in preferred embodiments, the present invention provides novel *Synechocystis* mutant pds gene(s) conferring resistance to 4'-fluoro-6-[(alpha,alpha,alpha,-trifluoro-m-tolyl)oxy]-picolinamide.

Also, in further preferred embodiments, the present invention provides a method of using a simple genetic system, *Synechocystis*, to select and isolate mutants forms resistant to 4'-fluoro-6-[(alpha,alpha,alpha,-trifluoro-m-tolyl)oxy]-picolinamide.

In additional embodiments, a method for the preparation of pds resistant nucleic acid fragments from the cyanobacteria *Synechocystis* EMS resistant cell lines is provided.

In additional preferred embodiments, the present invention provides novel *Synechocystis* mutant pds gene(s) conferring cross-resistance to known PDS inhibitors and 4'-fluoro-6-[(alpha,alpha,alpha,-trifluoro-m-tolyl)oxy]-picolinamide.

Another approach to the use of cyanobacterial genes for controlling plant traits is to use natural cyanobacterial genes, which already have desired characteristics. The acetolactate synthase (AHAS) enzymes from *Synechocystis* PCC 6803 and *Anabaena* PCC 7120 are naturally resistant to imidazolinone and other AHAS inhibiting enzymes. The AHAS genes from these cyanobacterium could therefore be used to transform crop species thereby conferring herbicide resistance.

These cyanobacterial mutant genes, isolated from cyanobacterial sources, can be useful not only for herbicide resistance but also as selectable markers for herbicide, fungicide and insecticide resistance genes as well as ouput trait genes, as a component for a selection systems when coupled with the imidazolinones and other herbicides. Such a selectable marker system for nuclear or plastidic transformation could be used for major monocot and dicot crops such as maize, wheat, barley, canola, rice, tobacco, and soybean.

Thus, the present invention provides for improvements to current methods for identifying and utilizing cyanobacterial genes for modifying plant traits including herbicide resistance. Improvements include methods for screening of compounds to identify novel herbicidal modes of action and identify novel herbicide resistance mutations.

Thus, in preferred embodiments, the present invention provides a nucleic acid fragment encoding a herbicide resistant acetolactate synthase (ahas) large subunit gene from the cyanobacterium *Synechocystis* PCC 6803 and was cloned from a genomic DNA library.

In further preferred embodiments, a nucleic acid fragment encoding a herbicide resistant acetolactate synthase (ahas) small subunit gene from the cyanobacterium *Synechocystis* PCC 6803 was cloned from a genomic DNA library.

In additional preferred embodiments, this invention provides cyanobacteria as an alternative source of ahas and pds genes for plant transformations, in particular genes encoding herbicide insensitive proteins, and elements of genes for control of expression in plastids.

The present invention also provides a method for the improved genetic transformation of *Synechocystis*.

Finally the present invention provides for the use of the cyanobacterial pds and ahas genes as a selectable marker for transformations, and as a means of selection with the imidazolinones and 4'-fluoro-6-[(alpha,alpha,alpha,-trifluoro-m-tolyl)oxy]-picolinamide for herbicide resistance.

Additionally provided for is a method for target site gene identification, specifically, protocols for "High-Through-Put" molecular manipulation of cyanobacteria *Synechocystis*. This High-Through-Put system allows us to determine the mode of action of commercial and/or novel compounds for which the mode of action is unknown.

The integration of the processes, along with the described improvements, of; screening for *Synechocystis* mutants resistant to herbicides, the preparation of genomic DNA from the mutants, the transformation of *Synechocystis* of fragments of mutant DNA, and the identification of tranformants which are conferred herbicide resistance from the DNA fragments, and the sequencing of the DNA fragment to identify the target of the herbicide, the mutation conferring herbicide resistance, combined provide for an improved method for identifying novel Mode of Action and mutations within genes for altered traits.

BRIEF DESCRIPTION OF THE FIGURES/DRAWINGS

Figure Legends

FIG. 1. Selection of true resistant mutants.

FIG. 2. Identification of *Synechocystis* resistance mutant. (Resistant colonies plated on 5 μM 4'fluoro-6-[(alpha,alpha,alpha,-trifluoro-m-tolyl)oxy]-picolinamide plates).

FIG. 3. Susceptibility test of wild type and 4'fluoro-6-[(alpha,alpha,alpba,-trifluoro-m-tolyl)oxy]-picolinamide, mutants of *Synechocystis* using the paper disc assay. (Inhibition of wild-type *Synechocystis* in paper disc assay).

FIG. 4. Dose-response curve of *Synechocystis* wild type and 4'-fluoro-6-[(alpha,alpha,alpha,-trifluoro-m-tolyl)oxy]-picolinamide resistant mutants after seven days of suspension culture.

FIG. 5. HighThroughPut (HTP) Target Site Gene Identification in *Synechocystis*.

FIG. 6. In vivo growth of *Synechocystis* PCC 7120 and *Anabaena* PCC7120 cultured in BG-11 media in the presence of increasing concentrations of PURSUIT® imazethapyr and OUST® sulfometuron methyl.

FIG. 7. In vitro activity of *Synechocystis* PCC 7120 and *Anabaena* PCC7120 AHAS with increasing concentrations of PURSUIT® imazethapyr and OUST® sulfometuron methyl.

FIG. 8. PURSUIT® imazethapyr Spray Test Results

FIG. 9. Amplification of aadA and snAHAS Fragments

FIG. 10. AHAS Enzyme Assays

FIG. 11. p12deltaNI construct, also known as pACBC 111

FIG. 12. p12deltaNII construct, also known as pACBC112

FIG. 13. p116I construct
FIG. 14. p116II construct
FIG. 15. List of Constructs, including p116

DETAILED DESCRIPTION

A. Rapid Plate Based Assay for Identifying Lead Compounds

A prerequisite to successful utilization of *Synechocystis* in target site gene discovery is the identification of compounds that affect the metabolism of this organism. To this end, we have developed and established a rapid plate based assay for screening compounds inhibiting phytoene desaturase (pds) activity. In preferred embodiments the present invention provides improvements in the methods utilizing cyanobacteria, a paper disc assay and a microtitre liquid test, for the screening of novel herbicidal modes of action and to identify novel herbicide resistance mutations. Screening can be performed in simple media, preferably BG-11 (Sigma, St. Louis Mo.), without the need to maintain axenic conditions. Furthermore, quantitative determinations can be made within one to three days.

Screens can be designed to identify inhibitors of other specific metabolic pathways, which are common only to photoautotrophic cyanobacteria and higher plants and not heterotrophic organisms such as other bacteria.

To identify a target site gene activity, two types of Bluegreen algae, *Synechocystis* PCC 6803 (American Type Culture Collection, Rockville, Md.) and *Anabaena* PCC 7120 (American Type Culture Collection, Rockville, Md.) can be used for the screen. One is grown in microtiter dishes in BG-11 medium supplemented with various concentrations of the test compounds. Inhibition of growth can be monitored by visual inspection after two to three days of culture. Quantitative growth measurements can be taken photometrically starting one day after inoculation.

Alternatively screens can be performed on agar plates with "lawns" of cyanobacteria and paper discs impregnated with test compounds. In this case, zones of inhibited growth around paper discs can be detected after two or three days.

To set up the assay, wild type cells of *Synechocystis* were mixed with equal volumes of 2× top agar and 2×BG-11 and overlaid on top of BG-11 agar plate. Cells normally appear in 3–5 days after plating. This method will yield an even and uniform lawn of cells. Upon solidifying, test compounds are then spotted on Whatman filter paper disc before being placed on agar plates. Four compounds can be tested on a single plate. Using this screening, in an example employing 160 different compounds, predominantly compounds of novel mode of action, have been tested on this microbe, and on average, 25% of the compounds show at least some activity.

EXAMPLE 1

Cyanobacterial Screening Process

Rapid plate based assay for screening lead compounds was developed as follows. First, either one of two types of bluegreen algae, *Synechocystis* PCC 6803 and *Anabaena* PC 7120 were grown in microtitre dishes containing BG-11 supplemented with various concentrations of 160 different test compounds. Alternatively, screens can be performed on agar plates with lawns of cyanobacteria and paper discs impregnated with test compounds.

Susceptibility of *Synechocystis* to 4'fluoro-6-[(alpha,alpha,alpha,-trifluoro-m-tolyl)oxy]-picolinamide was tested using a paper disc assay in which 4' fluoro-6-[(alpha,alpha,alpha,-trifluoro-m-tolyl)oxy]-picolinamide was spotted in a paper disc before being placed on a lawn of cells. In determining susceptability, the size of the zone of inhibition is indicative of the potency of the compound.

These experiments also established a dose-response curve. A lethal concentration for resistant mutant selection was 1–2 µM of 4'-fluoro-6-[(alpha,alpha,alpha,-trifluoro-m-tolyl)oxy]-picolinamide. Dose-response studies were also performed in 96-well microtiter plates on wild type and putative 4'fluoro-6-[(alpha,alpha,alpha,-trifluoro-m-tolyl)oxy]-picolinamide resistant mutants of *Synechocystis*. The growth of the culture was measured daily at an optical density of 690 nm.

A rapid plate based assay for screening and identifying active compounds is then performed. Wild type cells of *Synechocystis* are mixed with equal volumes of 2× top agar and 2×BG-11. The mixture is then overlaid on top of a BG-11 agar plate. Cells normally appear 3–5 days after plating. This method will yield an even and uniform lawn of cells.

After solidification of the agar, test compounds were spotted on Whatman filter paper discs, and then were placed on agar plates. Four different compounds were tested on a single plate. Using this screening method, 160 different compounds were tested, predominantly compounds of novel mode of action. On average, 25% of the compounds show at least some activity.

B. *Synechocystis* Mutant pds Gene

The protein phytoene desaturase (PDS, encoded by the gene pds) is the target of a number of commercially available bleaching herbicides. The simple cyanobacterial genetic system, *Synechocystis*, was used to generate and select mutant forms of pds resistant to bleaching herbicide 4'-fluoro-6-[(alpha,alpha,alpha,-trifluoro-m-tolyl)oxy]-picolinamide. (BASF (Previously American Cyanamid Company), Princeton, N.J.)

4'-fluoro-6-[(alpha,alpha,alpha,-trifluoro-m-tolyl)oxy]-picolinamide is a herbicide for the post-emergence control of broad leaf weeds in winter and spring wheat. Its site of action has been determined to be PDS. On BG-11 (Sigma, St. Louis Mo.) solid medium in a paper disc assay, 4'-fluoro-6-[(alpha,alpha,alpha,-trifluoro-m-tolyl)oxy]-picolinamide was found to be active against *Synechocystis* PCC 6803 (Referred to as *Synechocystis*) at concentrations in the 1–2 µM range. Furthermore, *Synechocystis* growth was inhibited with an $I_{50}$ in the lower sub-micromolar range when it was tested in liquid cultures.

Thus, the present invention provides novel *Synechocystis* mutant phytoene desaturase (pds) gene(s) conferring resistance to 4'-fluoro-6-[(alpha, alpha, alpha,-trifluoro-m-tolyl)oxy]-picolinamide.

The present invention provides a method to isolate and select mutants resistant to 4'-fluoro-6-[(alpha, alpha, alpha,-trifluoro-m-tolyl)oxy]-picolinamide. Two types of mutants may be isolated: spontaneously produced mutants or chemically induced mutants.

Spontaneous mutants were obtained by growing wild-type *Synechocystis* in liquid culture, or directly plated on plates containing lethal concentrations of 4'-fluoro-6-[(alpha,alpha,alpha,-trifluoro-m-tolyl)oxy]picolinamide or through stepwise exposure to increasing levels of 4'-fluoro-6-[(alpha,alpha,alpha,-trifluoro-m-tolyl)oxy]-picolinamide in liquid culture. Putative resistant colonies were then plated on selection plates to obtain single resistant cell lines.

For isolating chemically induced mutants, ethyl methanesulfone (EMS) may be used. *Synechocystis* cell cultures were treated with EMS at a concentration which gives a 99% killing rate, followed by growth on selection plates. 100–200 ml samples of logarithmic liquid culture were harvested and treated with EMS. The reaction was stopped by addition of sodium thiosulfate, to a final concentration of 5%, to quench excessive EMS. Cells were then collected and washed twice with BG-11. After an overnight recovery in fresh BG-11 medium, cells were plated on solid BG-11 medium containing 1 µM 4'-fluoro-6-[(alpha,alpha,alpha,-trifluoro-m-tolyl)oxy]-picolinamide.

Figure 1B:
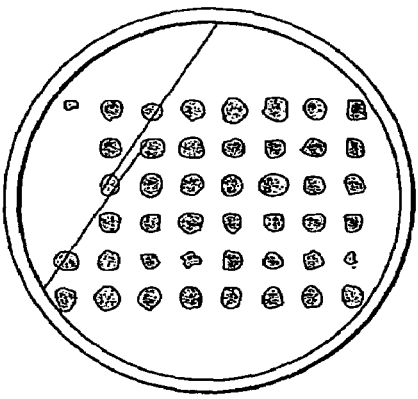
Figure 1C:
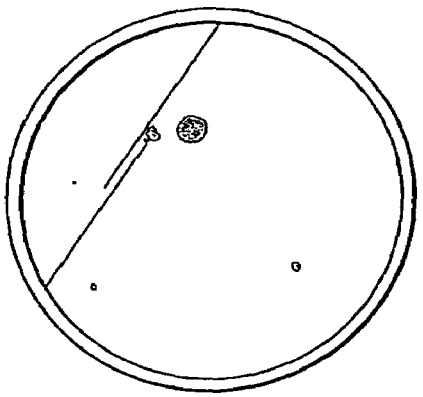
Figure 2A:
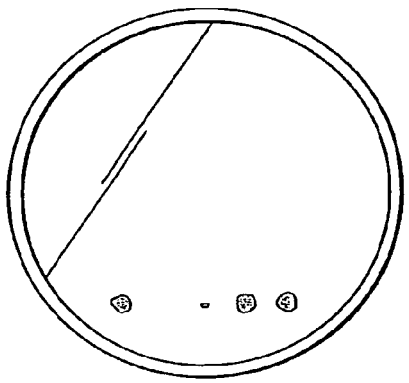
Figure 2B:
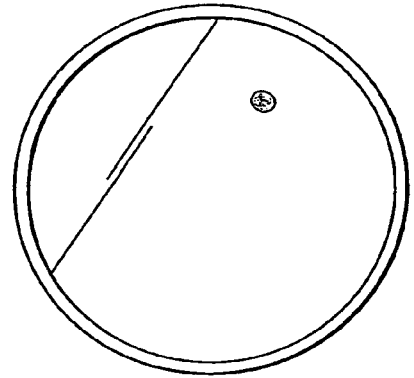
Figure 2C:
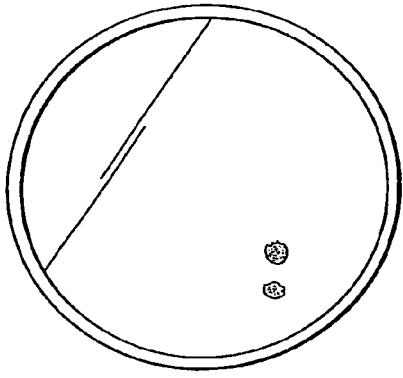
Figure 2D:
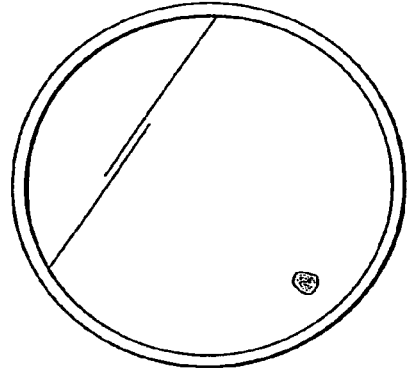

To select the 4'fluoro-6-[(alpha,alpha,alpha,-trifluoro-m-tolyl)oxy]-picolinamide resistant mutants, surviving colonies of the EMS treatment were picked and cultured in BG-11 in 96-well microtiter plates. After 2–4 days growth, cells were replica plated on BG-11 plates containing 0, 2, or 5 µM 4'-fluoro-6-[(alpha,alpha,alpha,-trifluoro-m-tolyl)oxy]-picolinamide to identify true resistant mutants. FIGS. 1A, 1B and 1C show the results from one set of selection plates. As the concentration of 4'-fluoro-6-[(alpha,alpha,alpha,-trifluoro-m-tolyl)oxy]-picolinamide was increased from 2 to 5 µM (from FIGS. 1B to 1C), the majority of the cells fail to grow. Out of 576 (96×6) putative resistant colonies plated on 5 µM of 4'-fluoro-6-[(alpha,alpha,alpha,-trifluoro-m-tolyl)oxy]-picolinamide plates, 7 resistant colonies were identified, as shown in FIGS. 2A, 2B, 2C and 2D.

The resistance phenotype of selected mutant cell lines was further tested in solid medium as well as in suspension cultures. Selected resistant colonies were given in-house names to differentiate themselves from one another: 5-1/12E, 5-1/12F, 7-2/1E, 7-3/11F, 7-3/12F, 7-4/12F. FIGS. 3*a*, 3*b*, 3*c*, 3*d*, 3*e*, 3*f* and 3*g* shows the growth of wild type *Synechocystis* was significantly inhibited at a rate of 4'-fluoro-6-[(alpha,alpha,alpha,-trifluoro-m-tolyl)oxy]-picolinamide as low as 0.5 nmol whereas the growth of mutant lines was inhibited at a substantially lesser rate. The difference between the wild type and mutant lines becomes even more apparent at the highest rate (5 nmol) tested.

In this particular experiment zones of inhibition for the wild type *Synechocystis* cells were observed at the two higher 4'fluoro-6-[(alpha, alpha, alpha,-trifluoro-m-tolyl)oxy]-picolinamide application rates ($5 \times 10^{-10}$ mol and $5 \times 10^{-9}$ mol) with a diameter of 20 and 38 mm, respectively. However, zones of inhibition were only observed with 4 of the 6 mutants at the highest rate of 4'fluoro-6-[(alpha,alpha,alpha,-trifluoro-m-tolyl)oxy]-picolinamide, results with degree of resistance in the following order: 7-3/11F(0)=7-4/12F(0)>5-1/12E(8)>7-3/12F(12)>5-1/12F(18)>WT(38) (size of zone in mm in parentheses).

In suspension cultures, all mutants exhibit increased resistance against 4'fluoro-6-[(alpha,alpha,alpha,-trifluoro-m-tolyl)oxy]-picolinamide. FIG. 4 shows the result from one such dose-response experiment after seven days of culture. For wild type cells (WT), the growth was inhibited at concentrations of 4'-fluoro-6-[(alpha,alpha,alpha,-trifluoro-m-tolyl)oxy]-picolinamide of <0.25 µM, with an 150 in the sub µM range. By contrast, the $I_{50}$ values are between 1–2 µM for 5-1/12E, 5-1/12F, and in the range of 5–10 µM for 7-3/12F and 7-4/12F, respectively.

Thus, there is substantial evidence that the isolated cell lines confer increased levels of 4' fluoro-6-[(alpha, alpha, alpha,-trifluoro-m-tolyl)oxy]-picolinamide resistance.

EXAMPLE 2

Isolation and Selection of Mutant PDS Genes

100–200 ml of logarithmic liquid culture was harvested and treated with mutagen ethyl methanesulfonate (EMS) in a phosphate buffer. To quench excessive EMS, the reaction was stopped with the addition of sodium thiosulfate to a final concentration of 5%. Cells were collected and washed twice with BG-11, then placed in a fresh BG-11 medium for overnight recovery.

The cells were then plated on a solid BG-11 medium containing 1 µM 4'fluoro-6-[(alpha,alpha,alpha,-trifluoro-m-tolyl)oxy]-picolinamide. Surviving colonies were cultured in BG-11 within 96-well microtiter plates.

To identify true mutants, cells were replica plated on BG-11 plates containing 0, 2 or 5 µM 4'fluoro-6-[(alpha,alpha,alpha,-trifluoro-m-tolyl)oxy]-picolinamide, after 2–4 days growth.

A result from one set of figure plates is shown in FIGS. 1A, 1B and 1C. As the concentration of 4'fluoro-6-[(alpha,alpha,alpha,-trifluoro-m-tolyl)oxy]-picolinamide was increased from 2 to 5 µM, the majority of the cells failed to grow. Only 7 resistant colonies were identified out of the 576 (96×6) putative resistance colonies plated on 4'fluoro-6-[(alpha,alpha,alpha,-trifluoro-m-tolyl)oxy]-picolinamide. FIGS. 2A, 2B, 2C and 2D.

The resistant phenotype of selected mutant cell lines was further tested in solid medium as well as in suspension cultures. For the solid medium tests, a paper disk assay was done. As shown in FIG. 3, the growth of wild type *Synechocystis* was significantly inhibited with 0.5 nmol of 4'fluoro-6-[(alpha,alpha,alpha,-trifluoro-m-tolyl)oxy]-picolinamide. In contrast, the growth of the mutant lines was inhibited at a lesser rate. The difference between the wild type cells and the mutant cell lines become more apparent with a higher concentration of 4'fluoro-6-[(alpha,alpha,alpha,-trifluoro-m-tolyl)oxy]-picolinamide.

In a suspension culture test, all mutants exhibited increased resistance against 4'fluoro-6-[(alpha,alpha,alpha,-trifluoro-m-tolyl)oxy]-picolinamide. FIG. 4 shows the result from one such dose response experiment after seven days. Wild type cells were inhibited at concentrations of <0.25 µM 4'fluoro-6-[(alpha,alpha,alpha,-trifluoro-m-tolyl)oxy]-picolinamide, with an $I_{50}$ in the sub µM range. In contrast $I_{50}$ values are between 1–2 µM fir 5-1/12E and 5-1/12F, and between 5–10 uM for 7-3/12F and 5-4/12F. Thus, because the cell lines with the mutant pds genes are far more resistant that wild type cell lines, there is evidence that the selected cultures contain 4'fluoro-6-[(alpha,alpha,alpha,-trifluoro-m-tolyl)oxy]-picolinamide resistance.

A method for the preparation of pds resistant nucleic acid fragments from the cyanobacteria *Synechocystis* EMS resistant cell lines is provided in additional preferred embodiments.

Genomic DNA was prepared from six *Synechocystis* EMS resistant cell lines obtained from the isolation and selection process above. A 1.7 Kb Genomic DNA fragment encompassing the pds was amplified using Genomic DNA as a template. PCR amplified pds gene fragments were subsequently subcloned into the Invitrogen TOPO TA Cloning vector pCR2.1-TOPO (Invitrogen Corp, Carlsbad, Calif.) to obtain plasmid pCR2.1-TOPO-PDS.

Cloning of the resistant pds gene into a vector was done as follows. A pair of primers were designed based on sequence information available in a database (database available at www.ncbi.nlm.nih.gov/cgi-bin/Entrez/ framik?db=Genome&gi=112 or www.kazusa.or.jp/cyano/kwd.html). The primers had the sequence (from 5' to 3'): X62574-5' cgaattccctggtagcatttaatacaattggc, identified as Sequence ID NO: 1 and X62574-3' cgcataagctttgcagatggagacggtttgggc, identified as SEQ ID NO: 2. The primers were used to amplify the pds gene encoding phytoene desaturase, using *Synechocystis* Genomic DNA (prepared from six *Synechocystis* EMS resistant cell lines obtained from the isolation and selection process above) as a template. A 1.7 Kb PCR fragment was obtained and subsequently subcloned into Invitrogen TOPO TA vector to generate plasmids TOPO TA-PDS (PDSr).

EXAMPLE 3

Cloning and Subcloning of Mutant PDS Gene

Cloning of the mutant pds genes went as follows. A pair of primers were designed to amplify the pads gene using *Synechocystis* DNA prepared from wild type and 4'fluoro-6-[(alpha,alpha,alpha,-trifluoro-m-tolyl)oxy]-picolinamide resistant mutant cells as templates.

PDS genes were cloned from wild type *Synechocystis* and 4'fluoro-6-[(alpha,alpha,alpha,-trifluoro-m-tolyl)oxy]-picolinamide resistant cell lines. *Synechocystis* genes were cloned from cell lines by a PCR based strategy. Genomic DNA was used as a template. Based on sequence information available in a database, the following primers were used (from 5' to 3'): X62574-5' cgaattccctggtagcatttaatacaattggc, SEQ ID NO: 1, and X62574-3' cgcataagctttgcagatggagacgtttgggc, SEQ ID NO: 2.

A 1.7 Kb PCR fragment was obtained and subsequently subcloned into Invitrogen TOPO TA vector, resulting in plasmids TOPO TA-PDS (PDSr). PCR products were subcloned into an Invitrogen TOPO TA cloning vector, generating TOPO TA-PDS (PDSr). Plasmids carrying pds insertion were prepared using Qiaprep Spin Miniprep Kit. (Qiagen Inc., Valencia, Calif.).

PDS gene PCR products as well as plasmids carrying pds gene derived from all six mutant cell lines were used in a functional complementation assay.

Testing was done to eliminate the possibility that 4'fluoro-6-[(alpha,alpha,alpha,-trifluoro-m-tolyl)oxy]-picolinamide resistance was linked to a mutation other than, or in addition to, the phytoene desaturase in *Synechocystis*. Digested *Synechocystis* genome DNA, PCR fragments of PDS gene and TOPO TA-PDSr plasmids were all used in a genetic complementation study. All DNA species tested transformed *Synechocystis* to 4'fluoro-6-[(alpha,alpha,alpha,-trifluoro-m-tolyl)oxy]-picolinamide resistance. This suggests that resistance to 4'fluoro-6-[(alpha,alpha,alpha,-trifluoro-m-tolyl)oxy]-picolinamide is associated with the mutation in the pds gene in these mutant cell lines.

Three independent clones were picked and sequenced for each mutant cell line. Sequencing of PCR amplified pds gene product from resistant cell line 7-4/12F revealed a single base pair change of G⇒A at position 642 (position 523 within ORF) (Table 1), resulting in an amino acid change of Ala⇒Thr at position 175. The sequence is identified as Sequence ID NO: 3. This mutation is unique and different from the only mutation (Arg$^{195}$⇒ Cys, Pro, or Ser) described in the pds gene from *Synechocystis* by [Sandmann et al., 1998], and four other point mutations (Arg$^{195}$⇒Pro, Leu$^{320}$⇒Pro, Val$^{403}$⇒Gly, Leu$^{436}$⇒Arg) previously reported for the pds gene from *Synechococcus* sp. PCC 7942. All of the previously described mutations were identified based on their ability to confer resistance to the commercial herbicide norflurazon to wild type cells.

TABLE 1

List of point mutations in herbicide resistance-conferring pds genes from cyanobacteria

| Amino Acid Position | Mutation | A.A. Substitution | Source | Target Herbicide | References |
|---|---|---|---|---|---|
| 175 | G⇒A | Ala⇒Thr | *Synechocystis* | 4'-fluoro-6-[(alpha,alpha,alpha,-trifluoro-m-tolyl)oxy]-picolinamide | This work |
| 195 | C⇒T | Arg⇒Cys | *Synechocystis* | norflurazon | Martínez-Férez & Vioque 1992 |
| 195 | C⇒A<br>C⇒T<br>G⇒C | Arg⇒Ser<br>Arg⇒Cys<br>Arg⇒Pro | *Synechocystis* | norflurazon | Martínez-Férez et al 1994 |
| 403 | T⇒G | Val⇒Gl | *Synechococcus* | norflurazon | Chamovitz et al 1991 |
| 195<br>320<br>436 | G⇒C<br>T⇒C<br>T⇒C | Arg⇒Pro<br>Leu⇒Pro<br>Leu⇒Arg | *Synechococcus* | norflurazon | Chamovitz et al 1993 |

EXAMPLE 4

Sequencing of Mutant PDS Gene

Three independent clones were picked and sequenced using the dRhodamine Terminator Cycle Sequencing Kit. (PE Biosystems, Norwalk, Conn.). The reactions were analyzed in an ABI A310 Genetic Analyzer (ABI, Foster City, Calif.) Sequencing the PCR amplified pds gene product from resistance cell line 7-4/12F revealed a single base pair change of G⇒A at position 642 (position 523 within ORF) See Table 1. The result is an amino acid change of Ala⇒Thr at position 175. The mutation is unique. It is different from the only mutation described in the pds gene from *Synechocystis* (ARG195⇒Cys, Pro or Ser), and four other point mutations previously reported for the pds gene from *Synechocystis* sp. PCC 7942 (Arg195⇒Pro, Leu320⇒Pro, Val403⇒Gly, Leu436⇒Arg). All of those mutations were identified based on their ability to resist commercial herbicide norflurazon to wild type cells.

The complete sequence of the novel mutant form pds gene, identified as SEQ ID NO: 3, reads as follows:

```
   1 ccctggtagc atttaataca aattggctat cttggcaaag tcccccgaaa tattacgaaa 61 cgtaaagtat aataacaatc aacctgtaaa ccccaaatgc cttagcgaga cagtaaccca 121 tgcgcgttgt gatcgccgga gccggattag ccggcctagc ctgtgccaaa tacttagccg 181 atgcgggctt taccccgtc gtcttggaac gtagggatgt attaggcggg aagatcgccg 241 cgtggaaaga tgaggacgga gattggtacg aaaccggcct acacattttt tttgggggcct 301 atcccaacat gttgcagtta tttaaggaat tggatatcga agatcgtctg caatggaaag 361 agcacagcat gatcttcaac caaccagaga aaccaggtac ctactctcgg ttcgattttc 421 cggatattcc ggcccccatc aatggtttgg tagccattct tcgcaacaac gatatgctta 481 cctggccgga gaaaattcgc tttggcttgg gactcttgcc ggccattgtc cagggccaga 541 gctatgtgga agaaatggat aaatacactt ggtcagagtg gatggccaaa caaaatattc 601 cccccgcat cgaaaaagaa gttttcattg ccatgagtaa g[a]cgttgaac tttattgatc 661 ccgatgaaat ttccgccacc attttactta ctgccctcaa tcgcttttta caggaaaaaa 721 atggctctaa gatggcattc ctggatgggg caccaccgga gcgtctttgc caacctttgg 781 tcgactatat tacggaacgg ggaggggaag tacacattaa taaacctctc aaagaaattt 841 tgcttaatga agatggttcc gttaagggtt acttaatccg gggcctagat ggagcccccg 901 acgaagtgat cacagcggat ttatatgtgt ctgccatgcc ggtggatccc ctgaaaacca 961 tggtgccagc gccctggaga gaatatcctg agtttaagca aatccaaggt ttggaaggag 1021 tcccggtcat taacctccac ctgtggtttg accgtaagtt aaccgacatt gatcatttgt 1081 tattctcccg atcgccgttg ttgagtgttt acgccgacat gagcaacacc tgccgagaat 1141 acagtgatcc agacaaatcc atgttggaat tggtgctggc tccggcccag gattggatcg 1201 gcaaatccga cgaagagatt gtggcggcca ccatggcgga gatcaagcaa ctctttcccc 1261 aacacttcaa cggggataat ccagcccgac tgcttaaatc ccacgtggtc aaaaccccc 1321 gctcagtcta caaagctacc cccggaaggc aggcttgtcg ccccgatcaa cggacatcgg 1381 tgcccaactt ttacctagca ggggacttca ccatgcaaaa atacttgggc agtatggaag 1441 gggcggtgct ttccggcaaa caatgcgccc aggcgatcgc cgccgatttc aacccccaaa 1501 ccgttcccc caccagggaa atagtcaccg tgggttaagc cgcctggact ccctggtaat 1561 cttcctgaca aatggcaacc ctaatgcgac aatgctaaat ggctaacggt caaatttctc 1621 cccagcgtgc agttaccaaa ccccaatcct ggtggctgac ttccgaaccc cgtccgtcct 1681 taatgttaca actgcccaaa ccgtctccat ctgcaaagcc ctgtgcttct gttga
```

The 5′ PCR primer with an engineered EcoR I (Promega) site was highlighted in bold, and that of the 3′ PCR primer with an engineered Hind III (Promega) site was also bold typed. The novel substitution of G→A at position 642 (position 523 within the PDS ORF) is boxed.

In further embodiments we provide a method for the improved genetic transformation of *Synechocystis*. In the literature, transformation of *Synechocystis* has been performed using either one of the two approaches, "in situ" dot transformation first reported by Dzelzkalns & Boogied (*The EMBO J.*, 1998, 7: 333–338), and liquid culture based transformation (ref. Williams, *Methods in Enzymology* 1988, 167: 766–778). For the liquid culture based procedure, DNA samples were mixed with fresh cells of *Synechocystis* and incubated for certain period of time before being spread onto membrane filters resting on BG-11 agar plates. After an extended incubation of the plates under standard conditions for the expression of inserted gene(s), the filters were transferred to plates containing selection agents. This is a lengthy procedure and may not be suitable for High-Through-Put transformation.

The "in situ" dot transformation procedure entails direct application of DNA sample (restriction fragments, cloned plasmids) in liquid or melted agarose onto a lawn of *Synechocystis* 6803 cells containing selection agents. It is quick and convenient, but cells were not given the time to express the inserted gene before being exposed to selection agents, this procedure is also "destructive" in that DNA samples will be lost regardless of transformation results.

*Synechocystis* DNA was prepared using the Qiagen Dneasy Plabt Mini Kit (Qiagen, Valencia, Calif.) following NaI pretreatment and digestion with lysozyme as describes in Williams (1988). For manipulation of DNA in *E. Coli*, standard recombination procedures were followed.

A much-improved method was developed in our laboratory to overcome the limitations of the 'in situ' dot transformation and the liquid culture based transformation methods. To transform *Synechocystis*, competent cells were arrayed in 96-well plates. The DNA species to be transformed were then added and mixed with the cells. The 96-well plates containing mixtures of DNA and cells were then placed in a Sumilon plate (Vangard International Inc., Taipei, Taiwan) moistened with wet sterile paper towels. Cells were replica-plated at various times onto selection plates containing various concentration of the same or different selection agents. This method is extremely suitable for performing transformations and screening of a large number of samples, such as with the High-Through-Put protocol in Section C.

Transformation of wild-type *Synechocystis* with either DNA species results in enhanced 4'-fluoro-6-[(alpha,alpha,alpha,-trifluoro-m-tolyl)oxy]-picolinamide resistance. This reinforces the notion that resistance in the original cell lines is the result of mutation within the pds gene.

Also provided for in preferred embodiments is 4'-fluoro-6-[(alpha,alpha,alpha,-trifluoro-m-tolyl)oxy]-picolinamide resistant mutants which show cross-resistance against other PDS inhibitors. These mutants, when tested against another herbicides which are PDS inhibitors, compound (2E)-2-[amino(benzylsulfanyl)methylene]-1-(2,4-dichlorophenyl)-1,3-butanedione and two of its analogs, pyridine, 2-[(3,3-dichloro-2-propenyl)oxy]-4-methyl-6-[[2-(trifluoromethyl)-4-pyrodinyl]oxy] and 1,2,4,5-benzenetetracarboxamide,N,N',N'',N'''-tetrakis[5-(benzoylamino)-9,10-dihydro-9,10-dioxo-1-anthracenyl], exhibited cross-resistance.

C. High-Through-Put Target Site Gene Identification Using *Synechocystis*

In this invention, we further describe the successful development of various protocols for High-Through-Put (HTP) molecular manipulation of *Synechocystis*. These include but not limited to procedures such as lead compound identification, generation and selection of resistant mutant, HTP genetic transformation and functional complementation. As a result, it is now possible to design a program for rapid and cost effective identification of target site genes using this microbe.

As illustrated in FIG. 5, a prerequisite to the successful implementation of this program is the identification and availability of lead chemicals active on this microbe. Resistant mutants can be generated and selected against the compound of interest using a chemical based approach. To isolate the resistance-conferring gene, one of the most commonly adopted practices has been the gel fractionation method. This method entails the following steps: (1) digestion of genomic DNA prepared from mutant cell cultures of *Synechocystis*, (2) fractionation of digested DNA on agarose gel and purification of DNA from gel slices, (3) identification of positive fraction through $1^{st}$ round of functional complementation, (4) construction of a gene library, (5) preparation of plasmid DNA from single colonies, and (5) identification of target gene in 2 round of of functional complementation. This is a very time-consuming process. There is a possibility that the resistance-conferring fragment may not be the right size for complementation assay and/or for subsequent subcloning into library vector. Consequently, the gene fragment of interest may never be found in the gene library. By contrast, a preferred embodiment of the High-Through-Put program requires the preparation of ~1800 primer pairs for amplification of 1800 overlapping 2-kb fragments (the size of the fragment, thus the total number of primers, may be altered for easy PCR amplification and HTP manipulation) to cover the complete genome of *Synechocystis* (~3.6 Mb). It entails rapid amplification of 1800 fragments using genomic DNA from *Synechocystis* mutant cell lines.

A size range of 1.5~3 kb would be ideal, both for PCR amplification and homologous recombination in *Synechocystis*. PCR products that are too small would compromise the efficiency of transformation in this microbe. On the other hand, it is more difficult to amplify bigger gene fragment using PCR. Some trial and error adjustment can be made as needed in a particular PCR system according to methods well known to those skilled in the art. This process can be adapted to any organisms (e.g. Yeast *S. cerevisiae* or other cyanobacteria) for which the whole genome sequence information is known and transformation through homologous recombination is feasible.

PCR products can then be used for HTP transformation of *Synechocystis* and functional complementation assay on various selection plates, using methods well-known to those skilled in the art. Gene(s) conferring herbicide resistance can then be identified based on the ability of its PCR products to confer herbicide resistance to wild type cells upon transformation. All of which can be performed using 96-well microtitre plates, in addition, only one round of transformation is needed to identify the resistance-conferring gene. Some major steps in this process are detailed below:

(1) Lead compounds identification: This can be done in a reasonably high through put manner using either the paper disc assay on solid BG-11 agar plate or 96-well microtiter plate as described in Section A and Example 1.

(2) Generation and isolation of resistant mutant(s): *Synechocystis* mutant(s) resistant to compound of interest can be generated chemically by treating cultures of *Synechocystis* with chemical mutagens (e.g. EMS). Procedures for performing such experiment are provided in Examples 2 & 3.

(3) Isolation of genomic DNA from resistant cell lines: Genomic DNA can be prepared from cultures of *Synechocystis* resistance cell lines using commercial kits (e.g. Qiagen Dneasy Plant Kit) as described in Section B.

(4) Primer design and PCR amplification of gene fragments from *Synechocystis*: Primer pairs for amplification of overlapping DNA fragments from *Synechocystis* can be designed with the assistance of a commercial software package (e.g. Vector NTI from InforMax, North Bethesda, Md.). Large-scale synthesis of primers can be done by a commercial vendor (e.g. Sigma-Genosys, The Woodlands, Tex.) in 96-well format. PCR amplification of ~1800 2-kb fragments (again, the size of the fragment, thus the total number of primers may be altered for easy PCR amplification and HTP manipulation) can be performed using genomic DNA prepared from mutant cell cultures as template following standard laboratory procedures, as explained in Section B.

(5) High Through Put genetic transformation and target site gene identification: Procedures for HTP genetic transformation and functional complementation assays have been described in Section B. Gene(s) conferring herbicide resistance can then be identified based on the ability of its PCR products to confer herbicide resistance to wild type cells upon transformation.

D. *Synechocystis* AHAS Genes

AHAS Physical Properties

Cyanobacteria are a particularly useful source of genes for enhancing crop performance due to their similarity, and ancestral connection, to plant chloroplasts. In particular, cyanobacterial genes may be useful for transformation directly into the chloroplast genome due to similarities in genetic elements. Similarities in cyanobacterial genes and proteins to those from chloroplasts can carry over to a shared susceptibility to herbicides. *Synechocystis* PCC 6803 was demonstrated to be susceptible to several known herbicides as shown in Table 2 as described in detail below.

TABLE 2

| Compound | Activity Rating (++ = highest) | Target Site |
|---|---|---|
| Maleic Hydrazide | ++ | Carotenoid Biosynthesis |
| Simazine | ++ | Photosynthesis |
| Fenuron | ++ | ? |
| Monuron | ++ | Photosynthesis |
| CMU | + | Photosynthesis |
| Desmedipham | ++ | ? |
| Bromoxynil | + | Photosynthesis/Respiration |
| Phenmedipham | ++ | ? |

In cases where cyanobacteria are susceptible, they are good organism for use in screening for mutations that confer resistance due to the readily available methods for genetic manipulation such as transformation, high throughput screening, liquid or agar based selection, replica plating, shuttle vectors, a small, and in some cases a completely sequenced, genome. The mutated gene sequences that are isolated after selection for resistance can be transformed into the nucleus or plastome of plants, or alternatively, the functional equivalent of identified mutations can be inserted into genes from plants or other organisms for use in transformations.

In some cases cyanobacteria are insensitive to herbicides, potentially due to differences in uptake, metabolism, or differences in the target protein. Consequently, genes from cyanobacteria may be useful in conferring herbicide resistance to plants of interest.

AHAS Biochemistry

The end products of the branched chain amino acid biosynthetic pathway (isoleucine, leucine, and valine) feedback inhibit Acetohydroxyacid synthase (AHAS) activity. Only the large subunit has catalytic activity.

It has been established in the literature for many years that microbial AHAS enzymes, in-vivo, exist as two distinct but physically associated protein subunits. The two polypeptides, a "large subunit" and a "small subunit" are expressed from separate genes. From the study of AHAS enzymes from microbial systems, two roles have been described for the small subunit: 1) the small subunit is involved in the allosteric feedback inhibition of the catalytic large subunit when in the presence of isoleucine, leucine or valine and, 2) the small subunit enhances the activity of the large subunit in the absence of isoleucine, leucine or valine. For example, the large subunit alone has a basal level of activity that cannot be feedback inhibited by amino acids. When the small subunit is added, the level of activity of the large subunit increases. If the small subunit is included with isoleucine, leucine or valine, the activity is below that of the basal level with large subunit alone.

Since activity of prokaryotic AHAS large subunits have been shown to be suboptimal in the absence of small subunits, the level of activity of the *Synechocystis* AHAS large subunit, and its ability to confer herbicide resistance, may be suboptimal without co-expression of a small subunit gene.

The sequence of the entire genome of the cyanobacterium *Synechocystis* PCC 6803 has been determined and published. When the genome of *Synechocystis* PCC 6803 was published, subsequent to cloning of the original AHAS large subunit gene a search was done on the genome for other AHAS genes. The search found an additional gene with a high degree of homology to AHAS sequences. This gene in *Synechocystis* is designated sll1981 and annotated as ilvB.

However, prior to the publication of ilvB, sequence, we cloned a novel *Synechocystis* AHAS Large Subunit Gene nucleic acid fragment cloned from a genomic DNA library of cyanobacterium *Synechocystis* PCC 6803. This original gene that was cloned is identified as slr2088 and annotated as ilvG. Susceptibility tests show that AHAS activity is resistant to imidazolinones such as PURSUIT® imazethapyr (BASF, formerly American Cyanamid, Princeton, N.J.) and sulfonylureas such as OUSTS sulfometuron methyl (DuPont, Wilmington, Del.).

In vivo resistance of cyanobacteria to PURSUIT® imazethapyr and OUST® sulfometuron methyl As a preliminary matter, *Synechocystis* PCC 6803 and Anabaena PCC 7120 were tested for susceptibility to PURSUIT® imazethapyr and OUST® sulfometuron methyl. AHAS genes which are resistant to these herbicides are excellent candidates for transformation in plant plastomes and nuclear genomes. Such transformants can be used in a weed control strategy using a combination of transgenic herbicide resistant crops and herbicides.

In vivo testing of *Synechocystis* PCC 6803 and *Anabaena* PCC 7120 was done by culturing the organisms in varying concentrations of the commercial herbicides. Both organisms demonstrated a high degree of insensitivity to the compounds (FIG. 6). No inhibition of growth was seen at concentrations of 100 µM PURSUIT® imazethapyr or 100 nM OUST® sulfometuron methyl after one week of culture in BG-11 media. For relative comparison purposes a concentration of 1 µM PURSUIT® imazethapyr in agar media is lethal to *Arabidopsis* plants.

In Vitro Resistance of Cyanobacterial Acetohydroxyacid Synthase to PURSUIT® Imazethapyr and OUST® Sulfometuron Methyl AHAS is the target site of both PURSUIT® imazethapyr and OUST® sulfometuron methyl herbicides. To determine if resistance to the herbicides is due to a natural resistance to inhibition of the acetohydroxyacid synthase enzymes from the cyanobacteria, or if it is due to alternative mechanisms (e.g. lack of entry into the cell), the in vitro activity of the AHAS enzyme in the presence of the herbicides was tested.

AHAS assays were performed with slight modification as described by Singh et. al (Singh B K, Stidham M A Shaner D L, 1988, Assay of acetohyrdoxyacid synthase from plants. Anal Biochem 171: 173–179).

Results from the in vitro assays (FIG. 7) demonstrates that both *Synechocystis* and *Anabaena* AHAS enzymes are insensitive to inhibition by the herbicides. The $I_{50}$ of plant AHAS enzymes are normally in the range of 1–2 µM for imidazolinones and 10 nM for sulfonylureas (Singh, B. K., Stidham, M. A., and Shaner, D. L., J. Chromatogr., 444, 251, 1988). No significant inhibition of the cyanobacterial AHAS enzymes was observed at concentrations of 100 µM PURSUITS imazethapyr and 100 nM OUST® sulfometuron methyl.

Figures 3, 4, 5, 6, 7:
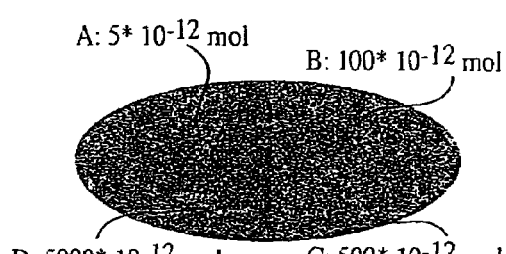
Figure 4:
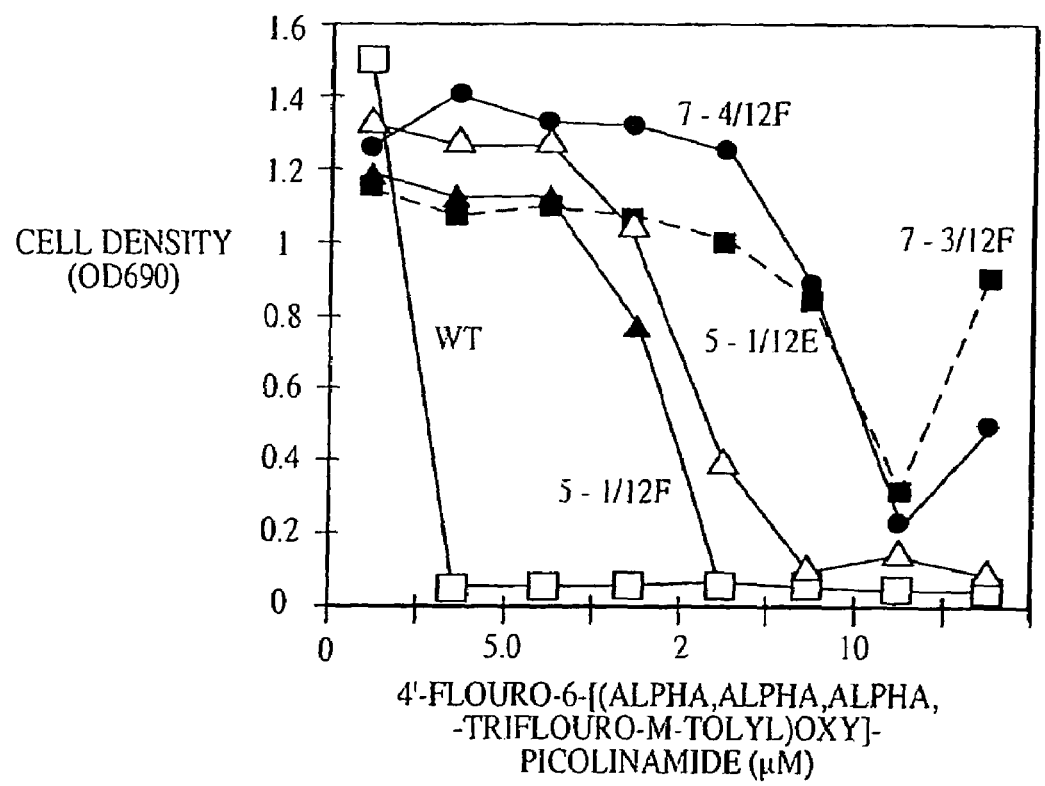
Figure 5:
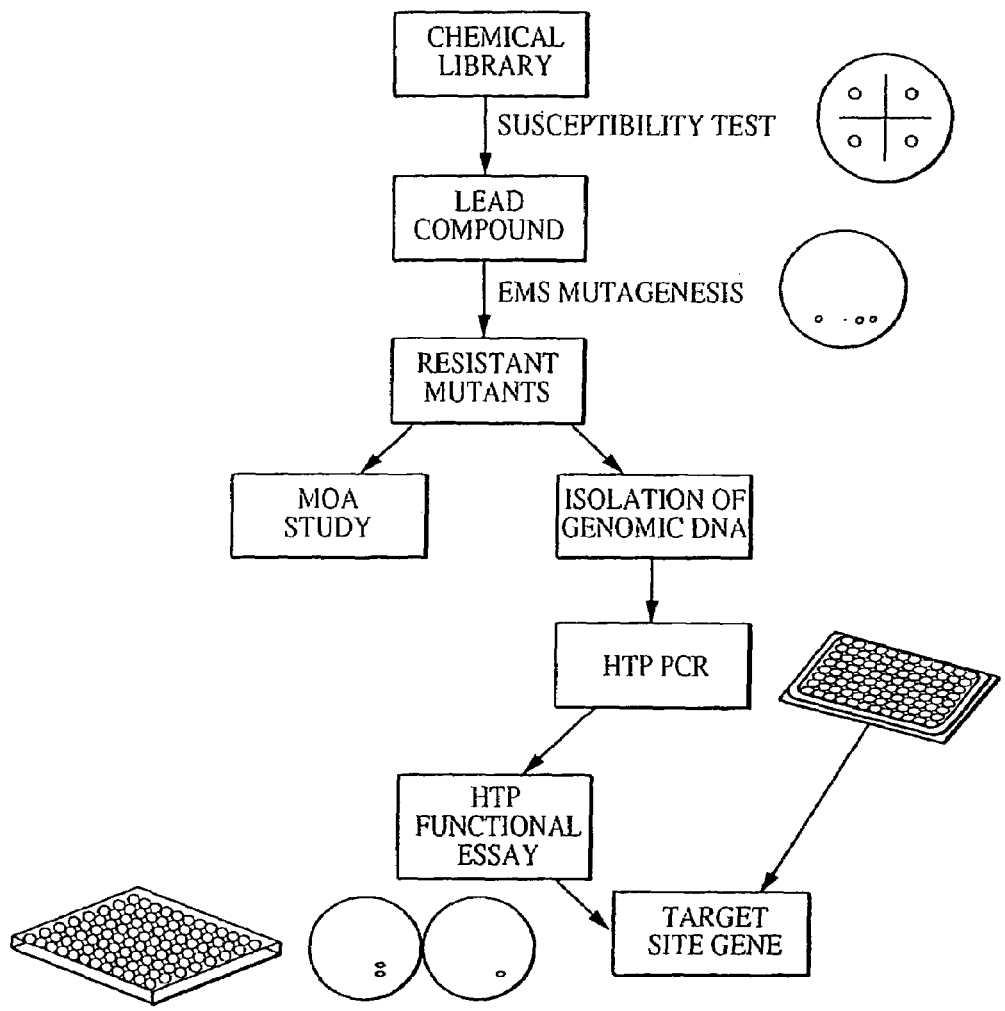
Figure 7:
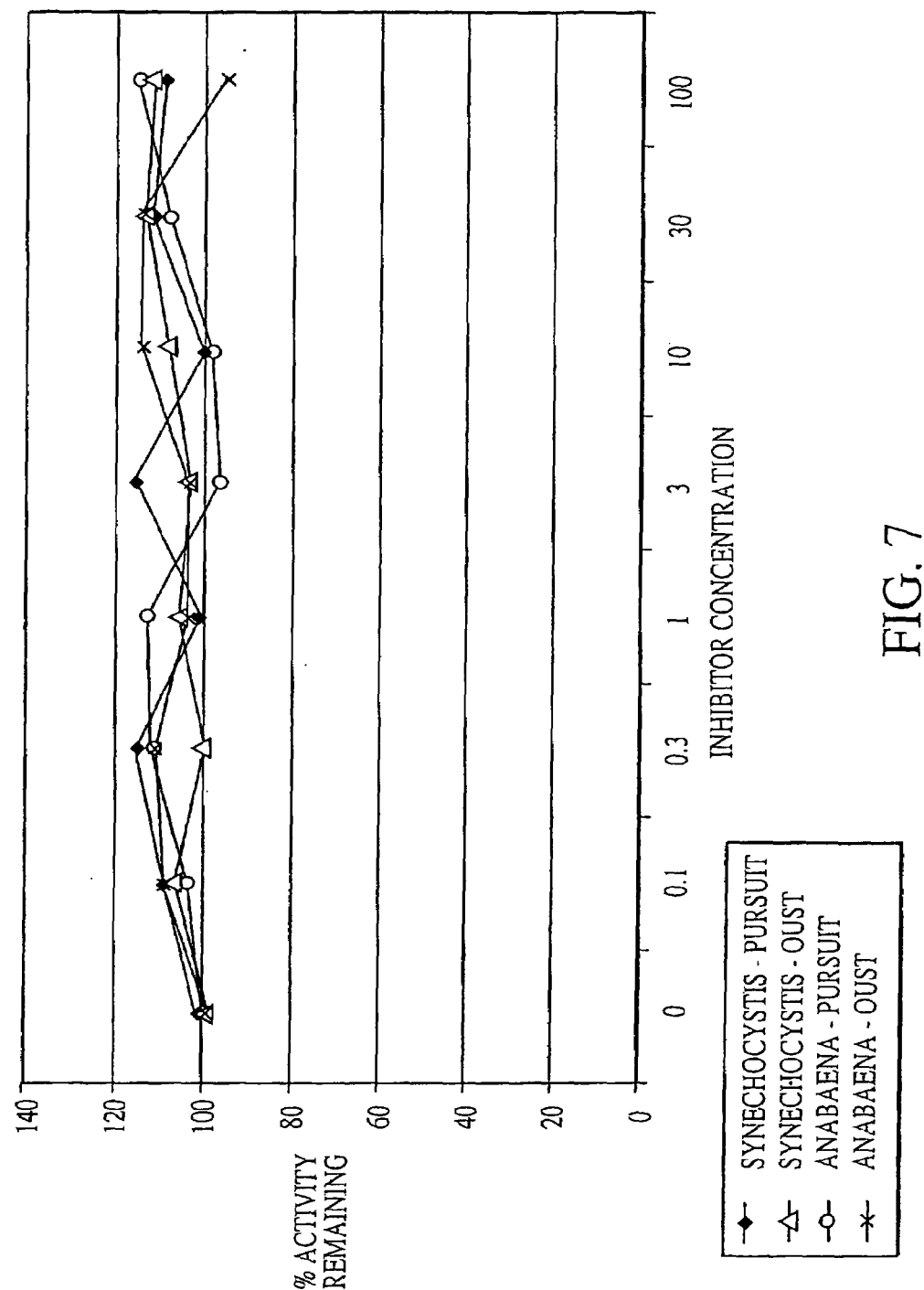

The data shown in FIG. 7 indicated that resistance to AHAS inhibiting herbicides could be attributed to the natural resistance of the target enzyme. Thus, cyanobacterial AHAS genes would be good candidates for transformation into plants, either by nuclear or plastid transformation, for conferring herbicide resistance.

Also, there is a level of cross-resistance exhibited between PURSUIT® imazethapyr and sulfanylcarboxamides. As discussed below, certain lines transformed with the p116 plasmid constructs (FIG. 9) described in detail below, when sprayed with 18 g/ha PURSUIT® imazethapyr showed about a 20% increase in plant resistance in the presence of PURSUIT® imazethapyr and sulfanylcarboxamides when compared with wild type tobacco. Interestingly, it appears that the *Synechocystis* AHAS enzyme displays a level of cross resistance to both PURSUIT® imazethapyr and sulfanylcarboxamides, although the herbicides are both quite dissimilar structurally.

EXAMPLE 5

In Vitro Resistance Resistance of Cyanobacterial Acetohydroxyacid Synthase to PURSUIT® Imazethapyr and OUST® Sulfometuron Methyl Experiments were done to determine in vitro resistance of cyanobacterial acetohydroxyacid synthase to PURSUIT® imazethapyr and OUST® sulfometuron methyl.

*Synechocystis* DNA was prepared using the Qiagen Dneasy Plabt Mini Kit (Qiagen, Valencia, Calif.) following NaI pretreatment and digestion with lysozyme as describes in Williams (1988). For manipulation of DNA in *E. Coli*, standard recombination procedures were followed.

The Bead Beater cell disrupter was packed in ice and turned on for 10 seconds, followed by cooling for 3 minutes. This cycles was repeated five times. The extract was transferred into a centrifuge tube, and spun in a Beckman SA20 (Beckman, Fullerton, Calif.) rotor for 15 minutes at 17,000 rpms.

The supernatant was decanted and used for AHAS assays. The assays were performed with slight modification as described by Singh et. al (Singh B K, Stidham M A Shaner D L, 1988, Assay of acetohydroxyacid synthase from plants. Biochem 171: 173:179). AHAS activity was assayed in a final concentration of 1×AHAS buffer, except HEPES was used instead of phosphate buffer that Singh used. All assays containing PURSUITS imazethapyr, OUST® sulfometuron methyl or associated controls contained a final concentration of 5% DMSO (Dimethyl Sulfoxide) due to addition of the herbicides to the assay mixtures as a 50% DMSO stock. Assays were performed in a final volume of 250 uL at 37° C. in microtiter plates for one hour.

Isolation of the *Synechocystis* AHAS Large Subunit Gene

The sequence of the coding and flanking regions of the isolated cyanobacterial AHAS gene of the present invention, which confers resistance to PURSUIT® imazethapyr AND OUST® sulfometuron methyl, was determined.

A probe for identifying the *Synechocystis* AHAS gene was generated by PCR with degenerate primers. To develop these degenerate primers, alignments were made of known AHAS sequences from plants, bacteria, and other cyanobacteria, such as *Spirulina platensis* (M75907.Gb_BA and M75906.Gb_BA, (GenBank, National Center for Biotechnology Information). It was found that the predicted amino acid sequences of AHAS protein shared many conserved regions. Thus primers were chosen in regions where amino acid sequences were highly conserved. Degenerate primers were used to allow for differences in the cyanobacterial codon usage. One of the primer pairs, identified as SEQ ID NO:4 and SEQ ID NO: 5, respectively had a sequence of:

(SEQ ID NO.4)
21:
5'GG(AGCT)AC(AGCT)GA(TC)GC(GACT)TT(TC)CA(AG)GA 3'

(SEQ ID NO.5)
19:
5'(CT)T(CG)CCA(CT)TG(AGCT)C(TG)(AGCT)ACCAT 3'

Genomic DNA was isolated from *Synechocystis* PCC 6803 (ATTC #27150) according to Methods in Enzymology 167, p 703–712 and was a template for PCR amplification of an AHAS fragment. The 1 kb PCR product corresponded in size to the fragment these primers would produce based on the distance between the two conserved regions from which the primers were designed. The fragment was isolated and cloned into the pCRII vector (Invitrogen). The insert was partially sequenced and the sequence was found to have strong homology to both of the *Spirulina* AHAS sequences (about 80% similarity and about 70% identity at the amino acid level between the *Synechocystis* sequence and the sequence from the M75907.Gb_BA and the *Synechocystis* sequence and the sequence from the M75906.Gb_BA *Spirulina*.)

EXAMPLE 6

Isolation of the *Synechocystis* Large AHAS Gene

A probe for identifying the *Synechocystis* AHAS gene was generated by PCR with degenerate primers. Genomic DNA was isolated from *Synechocystis* PCC 6803 according to the method outlayed in Methods in Enzymology 167, p/703–712. PCR was performed with DNA polymerase (Perkin Elmer AmpliTaq, Perkin Elmer, Shelton, Connecticut) using this genomic DNA as the template and a series of degenerate primers that were designed from the conserved regions observed in the alignment of AHAS gene sequences in Genbank. (www2.ncbi.nlm.nih.gov/genbank/query-_form.html). One of the primer combinations, identified as Sequence ID No.4 and Sequence ID No 5, respectively:

21:
5'GG(AGCT)AC(AGCT)GA(TC)GC(GACT)TT(TC)CA(AG)GA 3'

19:
5'(CT)T(CG)CCA(CT)TG(AGCT)C(TG)(AGCT)ACCAT 3' produced a 1.1 kb PCR product that corresponded in size to the fragment these fragments would produce, based in the sequences of the two AHAS genes from the cyanobacterium *Spirulina platensis*. The fragment was isolated and cloned in a pCRII vector (Invitrogen) The insert was amplified and partially sequenced, and was found to have strong homology to both of the *Spirulina* AHAS sequences, about 80% similarity, 70% identity at the amino acid level.

Library Screening

A genomic library from *Synechocystis* PCC 6803 in the Lambda ZAP vector (Stratagene, La Jolla, Calif.) was screened for the AHAS gene. To obtain the probe for screening the *Synechocystis* genomic library, the plasmid isolated in the above procedure was digested with Eco RI (Promega) and the resulting 1.1 kb fragment was gel isolated and purified (GeneClean, Bio 101, Qbiogene, Carlsbad, Calif.). This material (25–50 ng) was labeled with $^{32}P$ following the Oligolabelling Kit Standard Protocol (Pharmacia, Piscataway, N.J.). Thus labeled, the 1.1 kb fragment was used as a probe to screen for the AHAS gene in the Lambda Zap vector genomic library.

The *Synechocystis* PCC 6803 Genomic Library was plated on three plates (NZCYM media) (Sambrook, Fritsch, Maniatis "Molecular Cloning—A Laboratory Manual 2nd Ed" 1989) at a titer of $5 \times 10^3$ pfu/plate. Duplicate filters (BA-S NC, Schleicher & Schuell) were lifted from each of the plates. The filters were incubated on 15 cm 0.5N NaOH/1.5 M NaCl for 90 seconds, 0.5M Tris8/1.5 M NaCl for 5 minutes, and then 2×SCC (Sodium chloride, Sodium Citrate, pH 7.0) (Sambrook, Fritsch, Maniatis *Molecular Cloning—A Laboratory Manual* 2nd Ed. 1989) for 5 minutes.

The filters were then air dried and baked in a vacuum oven at 80° C. for two hours. Afterwards, the filters were prehybridized in 50 ml of prehyb solution (50% deionized formamide 5×SCC, 2× Denhardt's solution (Sambrook, Fritsch, Maniatis *Molecular Cloning—A Laboratory Manual* 2nd Ed. 1989), 0.1% SDS and 100 ug/ml salmon testes DNA) for 2 hours at 32° C. The filters were then hybridized overnight in a shaking water bath at 42° C. with the labeled probe.

The filters were washed with 2×SSC/0.2% SDS at 65° C. until it was determined that there was minimal radioactivity coming off in the wash solution. The filters were then blotted dry and exposed to X-ray film (Kodak XAR) (Kodak, Rochester, N.Y.) with image intensifying screens at −80° C. overnight.

A total of 38 duplicating positive plaques were picked and eluted into 1 ml of SM Buffer (0.1M NaCL, 0.008M $MgSO_4$ $7H_2O$, 0.05M Tris-HCl [ph 7.5], 0.01 gelatin.) Fifteen of the positives were then plated out (0.5 ml of a $10^{-4}$ dilution), and used for a second round of screening, using the same hybridization wash protocol as above. A single, well isolated hybridizing plaque was picked from each of the 15 positives and eluted into 1 ml SM solution. The phages were rescued into pBluescript (Lambda Zap II) using the ExAssist/SOLR System (Stratagene). Amplicillin resistant colonies were obtained from ten of the fifteen second round positive picks.

The subcloning process went as follows. The phagemid DNA obtained for the library screening process was labeled pSyn23/1. pSyn23/1 was double digested with the restriction enzymes Eco RI and Cla I (All restriction primers enzymes are available from Promega, Madison, Wis.) to produce a 3 kb fragment. The isolated fragment was ligated into pBluescript II (Stratagene, La Jolla, Calif.) and transformed into DH5alpha, (Stratagene) giving pSyn23/1-I. This AHAS clone was sequenced using the fmol DNA Sequencing System (Promega, Madison, Wis.) and a set of eight gene-specific primers plus the T3 sequencing primer located in the pBluescript II vector. An open reading frame of 625 amino acids was identified.

The resulting sequence of large subunit ilvG, identified as SEQ ID NO:6, had a sequence as follows:

| Acetohydroxy Acid Synthase (ilvG gene ORF) |
| --- |
| >Synechocystis sp. strain PCC6803 |
| GCCATAGGAGCCCATCGCCGATTGAGTTCAAATTAGAAGCACTTAGCCTA |
| CGCTTCCTAAACCGATTGTCCAGTGGTTGCATCAATTCCTAATCCCAAAA |
| CAAATTTCCTGAAAACTGTTCCTAGCCAACGGCAAACCGGGGCTTATATC |
| CTGATGGATAGCCTGAAACGCCATGGGGTCAAACACATTTTTGGCTATCC |
| CGGCGGGGCAATTTTGCCCATCTATGATGAACTGTACCGCTTTGAAGCGG |
| CGGGGGAAATTGAGCATATTTTGGTGCGCCATGAACAAGGAGCTTCCCAT |
| GCGGCGGATGGGTATGCCAGAGCCACAGGTAAAGTGGGAGTTTGTTTCGG |
| TACATCTGGACCAGGGGCGACTAACTTGGTGACCGGCATTGCCAATGCCC |
| ATTTGGACTCGGTGCCCATGGTGGTGATTACTGGAGAGGTGGGCCGTGCC |
| ATGATTGGTAGCGATGCTTTCCAGGAAATTGACATTTTTGGCATCACCTT |
| ACCGATCGTTAAGCACTCCTATGTGGTACGTAGTGCGGCGGATATGGCTC |
| GCATTGTTACTGAGGCTTTCCATCTTGCTAGCACCGGTCGTCCCGGCCG |
| GTTTTGATCGATATTCCCAAGGATGTGGGCTTAGAAGAATGTGAGTACAT |
| TCCCCTCGACCCCGGTGACGTTAATCTACCGGGTTATCGCCCCACGGTTA |
| AAGGTAATCCCCGACAAATTAATGCGGCATTGCAATTGTTGGAGCAGGCC |
| AGAAATCCCTTGCTCTACGTAGGGGGAGGGCGATCGCCGCCAATGCCCA |
| TGCCCAGGTGCAGGAATTTGCGGAAAGGTTCCAGTTGCCGGTAACAACCA |
| CCCTGATGGGAATTGGGGCTTTTGACGAAAACCATCCCCTTTCGGTGGGT |
| ATGTTGGGTATGCATGGCCACCGCTATGCCAACTTTGCCGTCAGCGAATG |
| TGATTTGTTGATTGCAGTGGGGGCCCGTTTCGACGACCGGGTAACTGGCA |
| AACTAGACGAATTTGCTAGCCGCGCCAAAGTAATTCACATTGACATCGAC |
| CCGGCGGAGGTGGGAAAAAACAGGGCTCCCGATGTGCCCATTGTGGGGA |
| TGTACGCCATGTTTTAGAACAGCTTTTGCAGCGGGCCCGGGAATTGGATT |
| ACCCCACCCATCCCCATACCACCCAGGCATGGTTAAATCGCATTGATCAT |
| TGGCGGACCGATTACCCCCTCCAGGTGCCCCACTATGAGGATACTATTGC |
| CCCCCAGGAGGTAGTACACGAAATTGGTCGCCAGGCCCCCGATGCCTACT |
| ACACCACCGATGTGGGACAACACCAAATGTGGGCGGCCCAGTTTTTGAAC |
| AATGGCCCCGCCGATGGATTTCCAGTGCTGGCTTGGGTACGATGGGCTT |
| TGGTTTACCTGCCGCCATGGGAGCCAAAGTGGGAGTGGGGGACGAGCGGT |
| CATTTGCATCAGTGGAGATGCCAGCTTCCAAATGAATCTTCAGGAACTGG |
| GAACCCTAGCCCAGTACGACATCCAGGTTAAAACTATTATTCTCAATAAC |
| GGTTGGCAGGGGATGGTGCGTCAGTGGCAACAAACTTTCTACGAAGAACG |
| TTATTCTGCTTCTAACATGTCCCAGGGCATGCCAGACATTAATCTCCTCT |
| GTGAAGCCTATGGCATCAAGGGTATTACTGTGCGCAAGCGGGAAGATTTG |
| GCCCCGGCGATCGCCGAAATGCTAGCCCACAATGGTCCTGTGGTGATGGA |
| TGTGGTGGTCAAAAAAGATGAAAACTGTTACCCTATGATTGCCCCCGGCA |

-continued

Acetohydroxy Acid Synthase (ilvG gene ORF)

TGAGTAATGCCCAAATGCTAGGTTTACCGGAAGTGCCGGTACNGGACAAT

GGTCCCCGGATGGTGGAGTGCAACCATTGCCAAACCCAAAATTTCATCAC

```
SYN1:  5' ATT GAG ATT TTT GGC ATC 3',       identified as SEQ ID NO: 7

SYN2:  5' TAT CCG CCG CAC TAC GTA C 3',     identified as SEQ ID NO: 8

SYN3:  5' CAG GGG CGA CTA ACT TGG TGA C 3', identified as SEQ ID NO: 9

SYN4:  5' ACC GCT ATG CCA ACT TTG CCG T 3,  identified as SEQ ID NO: 10

SYN5:  5' GGA GGA TAG TAC ACG AAA TTG G 3', identified as SEQ ID NO: 11

SYN6:  5' AAA TCT TCC CGC TTG CGC ACA G 3', identified as SEQ ID NO: 12

SYN7:  5' CCA ATT TCG TGT ACT ACC TCC TG 3', identified as SEQ ID NO: 13

SYN:8  5' AAA GTG GGA GTG GGG GAG GAA 3',   identified as SEQ ID NO: 14
```

-continued

Acetohydroxy Acid Synthase (ilvG gene ORF)

CCATCGTTTCTGTTCTGGTTGTGGAGCCAAACTCTAACCCATAAGCCAAA

ATTGAATTC

The predicted amino acid sequence of the open reading frame had 49% identity to the *E. coli* ilvG AHAS gene, 47% identity to the maize als2 gene, 46% identity to the *Arabidopsis* AHAS gene, and 65% identity to the sequence the AHAS gene from the cyanobacterium *Spirulina platensis*. The high degree of sequence identity and the functional demonstration of the cyanobacterial gene fragment in complementing the AHAS deficient *E. coli* mutants strongly suggest that the fragment represents a full length cyanobacterial AHAS large subunit gene.

To confirm that these plasmids carry functional AHAS sequences, plasmid DNA from each of the ten rescued colonies was transformed into the *E. coli* strain M1262. (leuB6, ilvI614, ilvH612, λ⁻, relA1, spoT1, ilvB619, ilvG603, ilvG605 (am), thi-1) (Genetics Stock Center, Yale University). This strain of *E. coli* is lacking in AHAS. Three of the plasmids were found to enable growth on M9 (+Leu) plates, thus indicating that these plasmids carried functional AHAS copies. *E. coli* M1262 expressing the cyanobacterial ahas gene were capable of growing on minimal media in the presence of OUST® sulfometuron methyl and PURSUIT® imazethapyr herbicides. The ahas gene can therefore be used for achieving herbicide tolerance in crops by transformation into the nuclear or plastidic genome.

EXAMPLE 7

Cloning and Sequencing the Large *Synechocystis* AHAS Gene

The phagemid DNA from one of the complementing lines pSyn23/1 was doubly digested with the restriction enzymes Eco RI and Cla I (Promega) to produce a 3 kb fragment. The Eco RI and Cla I were excised out of the pBluescript phagemid as the The isolated fragment was litigated into pBluescript and transformed into DH5alpha (Stratagene), creating pSyn23/1_I.

The resulting AHAS clone was sequenced using the fmol DNA Sequencing System (Promega) and a set of eight gene-specific sequencing primers:

Additionally, a T3 sequencing primer located in the pBluescript II vector was added.

An open reading frame (ORF) of 635 amino acid was identified. The predicted amino acid sequence of the open reading frame had 49% identity of the *E. coli* ilvg AHAS gene, 47% identity to the maize als2 gene, 46% identity to the *Arabidopsis* AHAS gene, and 65% identity to the sequence of the AHAS gene from the cyanobacterium *S. plantensis*.

Cloning of the AHAS Small Subunit from *Synechocystis*

In another embodiment of the present invention, a *Synechocystis* AHAS Small Subunit nucleic acid fragment was also cloned from a genomic DNA library of cyanobacterium *Synechocystis* PCC 6803.

Database searches of the complete genomic sequence of *Synechocystis* revealed three different ORFs encoding genes of acetolactate synthase, ilvG, ilvb, and ilvn. Further sequence similarity comparisons suggested that ilvn is likely to encode the small subunit of *Synechocystis* AHAS. To clone ilvn from *Synechocystis*, a PCR-based approach was adopted. Based on the sequence data, a pair of primers with the following sequences were designed, primer #1 (forward primer): 5'-cggtggaattttaccccaatgg-3', identified as SEQ ID NO: 15 and primer #2 (reverse primer): 5'-ggccctaaaacttggattccagg-3', identified as SEQ ID NO: 16 and these primers were used to PCR amplify the corresponding ORF (ilvN) from genomic DNA prepared from wild type cell cultures of *Synechocystis*.

Agarose gel analysis of PCR products yielded a band with the expected size (573 bp). PCR products have subsequently been subcloned into the Invitrogen TOPO pCR2.1 TA vector.

The gene was sequenced using the same procedures as above.

The resultant *Synechocystis* sp. strain PCC6803 revealed the sequence, identified as

SEQ ID NO: 17:

GTGGAATTTTACCCCAATGGCCACCGGCGATCGCCTTCTTTGCCCCCCAT

GAAACACACCCTCTCTGTTTTAGTTGAAGATGAAGCCGGAGTGCTAACCC

GCATTGCCGGACTATTTGCCCGCCGTGGTTTTAACATTGAGAGCTTGGCG

GTGGGGTCGGCGGAACAGGGGGACGTTTCCCGCATCACCATGGTGGTGCC

GGGGGATGAGAACACCATCGAACAACTGACCAAGCAACTCTACAAGTTGG

TTAACGTAATTAAAGTACAGGACATCACCGAAACTCCCTGTGTGGAAAGG

GAATTGATGCTGGTGAAGGTGAGCGCCAATGCCCCTAACCGAGCGGAAGT

GATTGAGCTAGCCCAGGTATTCCGGGCCCGCATTGTGGATATCTCCGAAG

ACACCGTCACCATCGAATGGTGGGGACCCGGGTAAAATGGTAGCAATCC

TCCAGATGTTGGCCAAGTTGGCATTAAAGAGGTGGCTCGAACGGGCAAAA

TTGCTTTGGTGCGGGAATCCGGCGTCAATACGGAATATCTGAAATCCCTG

GAATCCAAGTTTTAG

Construction of a Nuclear Plant Transformation Vector

Transformation of the AHAS genes into the nuclear genome required a nuclear plant transformation vector. Since branched chain amino acid biosynthesis is localized in the chloroplast in higher plants, for functional expression of AHAS in higher plants, the prokaryotic *Synechocystis* AHAS large subunit gene would need to be both expressed off of a plant expressible promoter and the protein would need to be targeted into the chloroplast. Therefore, a leader peptide will have to be fused onto the *Synechocystis* AHAS for it to be functional in the nuclear genome. When the gene is imported into the chloroplast, the leader peptide gets clipped. The final result would be the *Synechocystis* AHAS gene within the chloroplast minus the transit sequence.

Because the *Synechocystis* AHAS lacks the leader or transit protein sequence required to be active in the nuclear genome and transported into the chloroplast, the promotor and transit sequence of another organism was fused with the *Synechocystis* AHAS gene.

The promoter and transit sequence from the *Arabidopsis* AHAS large subunit was chosen to be fused to the *Synechocystis* AHAS large subunit gene, as there was a large degree of homology. The *Arabidopsis* genome has been sequenced and the physical and sequence information for AHAS large subunit can be found at the website provided by the *Arabidopsis* Information Resource. One skilled in the art could use the information at this database to perform the cloning as follows. The final result would contain the promoter and transit sequence of the *Arabidopsis* AHAS gene, followed by the *Synechocystis* gene, followed by the *Arabidopsis* terminator. The source of the promoter and transit sequence was the construct pAC793, (which consisted of a vector and an insert with a genomic fragment containing *Arabidopsis* AHAS promoter, transit sequence, coding region, and terminator.)

An alignment of the *Synechocystis* and *Arabidopsis* AHAS large subunits was made using the Gap program from Genetics Computer Group Inc. (GCG, Inc., Madison, Wis.) A region of homology near the N-terminal of the *Synechocystis* AHAS gene and past a putative transit sequence processing site on the *Arabidopsis* AHAS gene was chosen to make a fusion between the *Arabidopsis* transit sequence and *Synechocystis* AHAS. A common Eco RV restriction site in both the *Arabidopsis* and *Synechocystis* AHAS gene that was within a conserved region of the proteins was used as the fusion site. An Age I restriction site occurs naturally in the *Arabidopsis* gene. The site was found to be past the processing site and just past the stop codon of the *Arabidopsis* AHAS gene. Thus, it was chosen to create a fusion between the C-terminal end of the *Synechocystis* AHAS gene and the *Arabidopsis* AHAS termination sequence by insertion of an Age I site in the *Synechocystis* gene in a region homologous with the *Arabidopsis* gene.

PCR primers were designed to insert an Age I (primer SYNAGE) restriction sites on the 3-prime end of the *Synechocystis* AHAS gene. pAC793, a construct cloned from *Arabidopsis* abd contains genomic AHAS in a pGEM vector (Promega), was cut with Eco RV and Age I to remove most of the coding sequence of the *Arabidopsis* AHAS gene from the vector. The construct pSyn 23/1_I which contain a subcloned genomic fragment from *Synechocystis* (an Eco RI—Cla I subclone from the plasmid pSyn 23/1. pSyn23/1 was the resulting plasmid from screening the *Synechocystis* genomic library, first paragraph of this section. PSyn 23/1-1 was created by digesting pSyn 23/1 with Eco RI and Cla I and purifying the resulting fragment. The fragment was then ligated into pBluescript II that had been previously cut with Eco RI and Cla I.) that contained the entire AHAS gene was cut with Nco I and Age I to confirm that the correct fragment was obtained.

Using the pSYN 23/1_I vector as a template a PCR reaction was carried out with the primers. The reactions gave an expected 1.9 kb PCR fragment when run out on a 0.8% TAE agarose gel. The fragment was cloned into the TA cloning vector (TA cloning kit, Invitrogen) using a Ready-To-Go ligation vial (Pharmacia). The ligation products were transformed into competent cells from the TA cloning kit (Invitrogen).

The cells were gently transferred SOC media (Qbiogene, Carlsbad, Calif.) then gently transferred to a sterile culture tube and incubated. The cells were then plated on a blue-white media and incubated overnight at 37° C. The following day white colonies were selected.

Plasmid minipreps were made from cultures of selected white colonies. Restriction digestion of the plasmids generated expected fragments on agarose gels. The construct containing the fusion of the *Arabidopsis* AHAS large subunit promoter and transit sequence, the *Synechocystis* AHAS large subunit coding region, and the *Arabidopsis* AHAS large subunit termination sequence in the pGEM vector of the pAC793 vector, was labeled pGEKI. This construct could then be used for nuclear genome transformation where the *Synechocystis* AHAS gene is to be transported from the genome into the chloroplast.

EXAMPLE 8

Creation of a Nuclear Plant Transformation Vector

A nuclear plant transformation vector was constructed as follows. PCR primers were designed to insert Eco RV (primer SYNR5) and Age I (primer SYNAGE) restriction sites on the 5-prime and 3-prime ends, respectively, of the *Synechocystis* AHAS gene. They are identified as Sequence ID No. 18 (SYNR5) and Sequence ID No. 19 (SYNAGE). pAC793 was cut with Eco RV (just past the transit sequence) and Age I (just past the stop codon) to remove most of the coding sequence of the *Arabidopsis* AHAS gene from the vector. The remaining 7 kb fragment containing the pGEM vector, the *Arabidopsis* AHAS promoter, the transit sequence and the termination sequence was removed from an agarose gel and treated with phenol:chloroform:isoamyl alcohol washes. The fragment was cut again with Eco RV and Age I to make sure restriction digests were complete. The constructpSyn 23/1_I was obtained that contained a subcloned genomic fragment from *Synechocystis* (an Eco RI—Cla I subclone from the plasmid pSyn 23/1) which in turn contained the entire AHAS gene cut with Nco I and Age I to confirm that the correct fragment was obtained.

PCR primers were designed to insert an Age I (primer SYNAGE) restriction site on 3-prime end of the *Synechocystis* AHAS gene. A 5 prime primer was designed to amplify the gene upstream of the Eco RV site.

SYNR5: 5'-GGC TGA TAT CCT GAT GGA TAG CCT G-3', identified as Sequence ID No. 18

SYNAGE: 5'-TTG GCT TAC CGG TTA GAG TTT GGC TCC ACA-3', identified as Sequence ID No. 19.

Using the pSYN 23/1_I vector as a template, a PCR reaction was carried out with the primers. The reactions (35 cycles of 94° C. melting, 55° C. annealing and 72° C. polymerase elongation (Perkin Elmer Thermocycler) gave an expected 1.9 kb PCR fragment when run out on a 0.8% TAE agarose gel.

Two uL of the PCR reaction was diluted 8×. The TA cloning vector (TA cloning kit, Invitrogen) was resuspended in 8.8 ul of TE. (Tris/EDTA. Sambrook, Fritsch, Maniatis *Molecular Cloning—A Laboratory Manual* 2nd Ed. 1989). Two uL of TA cloning vector was added to a ligation vial (Ready-To-Go, Pharmacia). Additionally, one uL of 8× diluted PCR amplified fragment was added to the solution. Sterile water was added to bring the volume up to 20 uL. Without mixing, the vial was kept at room temperature for five minutes. After 5 minutes, the solution was mixed gently by sucking the solution in and out of a pipette tip. The sample was briefly spun to bring the solution to the bottom of the tube. The vial was then placed in a 16° C. water bath for 45 minutes.

Two uL of Beta-mercaptoethanol was added to each vial of competent cells provided in the Invitrogen TA cloning kit (Invitrogen). After 45 minutes in the ligation reaction, the vials were placed in ice for 3 minutes. Two uL of the ligation mix were added to the competent cells. The vial were then incubated on ice for 30 more minutes, followed by 60 seconds of heat shock at 42° C. The vials were again placed on ice for 3 minutes.

The cells were gently transferred to 450 μL of room temperature SOC media (Qbiogene, Carlsbad, Calif.) then gently transferred to a sterile culture tube and incubated by an hour of shaking at 225 RPM at 37° C. The cells were then plated on LB/amp/X-gal (Sigma) (Sambrook, Fritsch, Maniatis *Molecular Cloning—A Laboratory Manual* 2nd Ed. 1989) plates and incubated overnight at 37° C. The following day white colonies were selected.

Plasmid minipreps were made from cultures of selected white colonies. Restriction digestion of the plasmids generated expected fragments on agarose gels.

The construct containing the fusion of the *Arabidopsis* AHAS large subunit termination sequence in the pGEM vector was labeled pGEK1.

Nuclear Transformation of Cyanobacterial Genes into Plants

Agrobacterium Vector Construction

Tobacco plants were transformed with the *Arabidopsis/Synechocystis* AHAS fused gene. The vector pGEKI was cut with Kpn I and Sal I to remove the entire AHAS fused gene from the PGEM vector and was ligated into a pBIN19 *Agrobacterium* vector (Stratagene) that was previously cut with the same enzymes. Restriction analysis indicated that the fusion gene from pGEKI was successfully moved into the plant transformation vector.

Plants were selected on 100 mg/L kanamycin. Tobacco cultivar, Wisconsin-38 (North Carolina State University, US Tobacco Germplasm Collection) was grown aseptically on MSh⁻ medium (Sigma) containing sucrose (20 g/L) in glass (1 qt.) jars. Stem segments from plants 8–10 week were transferred to new jars for leaf propagation. Total DNA was extracted from tobacco lines using the Qiagen DNeasy Miniprep kit. (Qiagen, Inc., Valencia, Calif.).

Tests showed the transformants had little resistance to imidazolinone herbicides. This may have been due to several reasons. One reason may be that the *Synechocystis* AHAS large subunit was not accompanied by an AHAS small subunit. It has been shown that microbial AHAS genes are comprised of a large and small subunit. The large subunit of AHAS from *E. coli* does not have optimal activity in the absence of the corresponding small subunit. Since *Synechocystis*, similar to *E. coli*, is a prokaryotic organism it may share the same requirement. The absence of the small subunit may have diminished the activity of the enzyme and the ability to confer imidazolinone resistance.

Another potential reason for lack of resistance may have been the selection of the position of the fusion junction between the *Arabidopsis* AHAS transit sequence and the *Synechocystis* large subunit. An improper fusion junction may have produced a protein that either could not be localized in the chloroplast or produced a non-functional protein.

Plastid Transformation

It is believed that chloroplasts in higher plants were derived from cyanobacteria. The ancestral relationship between chloroplasts and cyanobacteria suggests that genes, gene elements, proteins, and many other features of the organisms are similar and potentially cross-functional. Cyanobacterial genes and gene elements may therefore be functional when transformed into plastid genomes. Moreover, expression of proteins from plastidic genomes obviates the need for transit sequences to traffic the protein to the proper location.

Therefore, use of cyanobacterial genes, or mutant genes isolated from resistant strains, for achieving herbicide resistance can be obtained by transformation into the plastome. Transgenes from alternative sources will confer different characteristics of the expressed traits. Regulatory elements of cyanobacterial genes can be used for control of expression in plastids. If a transgene is located in the plastome of a crop, its transfer to related species (weeds and/or crops) via pollination is prevented. The transgene will be expressed from a high number of copies per cell suggesting very high levels of expression. Furthermore, The location of transgene in the plastome obviates transport of gene products into the plastids and cyanobacterial genes can be used without modification of the coding region.

Thus, in preferred embodiments this invention provides cyanobacteria as an alternative source of genes for plant transformations, in particular genes encoding herbicide insensitive proteins, and elements of genes for control of expression in plastids. Furthermore, since sequenced DNA fragments contain prokaryotic regulatory elements, cyanobacteria can be directly used for plastome targeted transformations.

Specifically, the *Synechocystis* AHAS large subunit gene was used for transformation into plant chloroplasts to confer herbicide resistance.

Plastidic Transformation of Cyanobacterial Genes into Plant Chloroplasts

Figure 15:
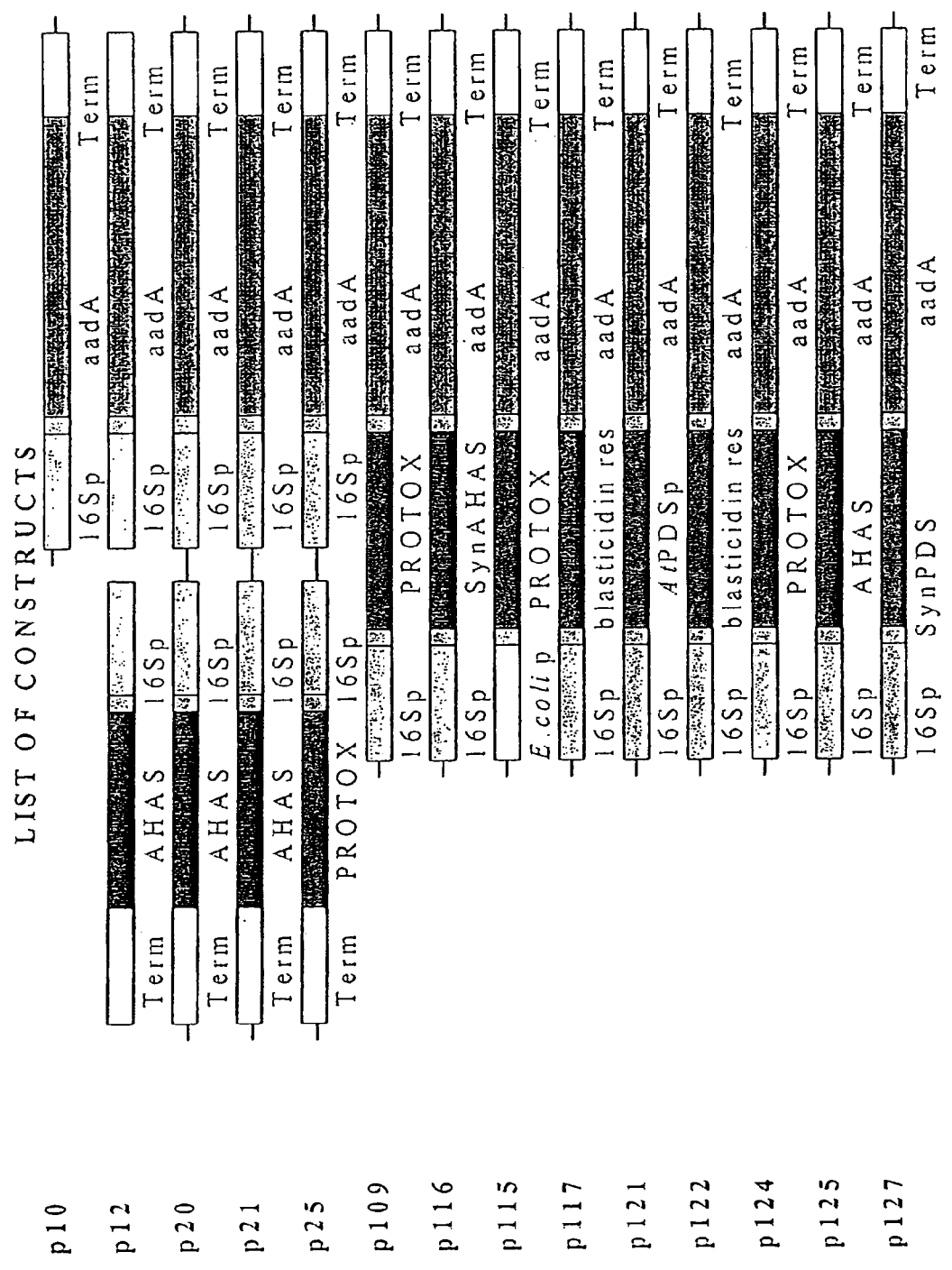

The genes were constructed into vectors to permit incorporation into and expression in the chloroplasts. The following vectors were constructed for transformation into plastid genomes. pACBC111 and pACBC112 are related constructs differing only in the orientation of the *Synechocystis* AHAS expression cassette. These vectors were constructed as shown in FIGS. 11 and 12. The aadA sequences and the p16S expression cassette are derived from the sequences described in U.S. Pat. No. 5,877,402 (Maliga et al.). The disclosure of this patent is incorporated by reference herein in its entirety. pACBC 111 is the same vector as p12 delta NI. pACBC112 is the same vector as p12 delta NII. p116 I (FIG. 13) is the same as pACBC222 and p116 II (FIG. 14) is the same as pACBC223. pACBC111 (or p12 delta NI) and pACBC112 (or p12 delta NII) are constructs where the *Synechocystis* AHAS gene and the aadA gene are expressed from individual promoters (FIGS. 11 and 12) The p116 I and p116 II are discistronic constructs, one promoter expressing an operon with two genes (Syn AHAS and aadA) differ from each other only in the orientation of the *Synechocystis* AHAS expression cassette (FIG. 15). The 222 and 223 vectors and the 111 and 112 vectors differ in that the p222/223 constructs are designed to express a dicistronic message while the p111/112 constructs will express the gene from a monocistronic insert.

Transformation and Regeneration of Transplastomic Plants

Plasmids pACBC222, pACBC111 and pACBC112 were used for plastid transformations. Leaves were cut and placed abaxial side down on regeneration medium (Msh⁻ medium supplemented with zeatin (2 mg/L), 1-naphthaleneacetic acid (0.1 mg/L), and sucrose (20 g/L).

Bombardments were carried out using the DuPont PDS 1000He Biolistic gun. (DuPont, Wilmington, Del.). Rupture discs (900 psi) (BioRad, Hercules, Calif.) were used, and helium pressure and vacuum levels were 1100 psi and 27" Hg, respectively.

Two days after bombardment, leaves were cut into 1 cm$^2$ pieces and placed on Spectinomycin (500 mg/L). Expanding and regeneration leaf segments were passed for up to 4 rounds on selection media. Fourth round regenerates were transferred to Magenta boxes (Sigma, St. Louis, Mo.) until sufficient roots were exhibited to warrant transplantation to the greenhouse.

EXAMPLE 9

Plastid Transformation

Plasmids p116, p12delta NI and p12delta NII were used for plastid transformations in the transformation and regeneration of transplastomic plants. Leaves were cut and placed abaxial side sown on regeneration medium (Msh⁻ medium supplemented with zeatin (2 mg/L) (Sigma), 1-naphthaleneacetic acid (0.1 mg/L), and sucrose (20 g/L). Gold was prepared for transformation by weighing 5 mg of gold (0.6 um) into Treff tubes (Treff A G, Degersheim, Switzerland) and washing once with both ETOH (100%) and sterile bidistilled water. The gold was pelleted and re-suspended in 230 uL water and mixed with 20 ug DNA (p 116, p12delta NI, or p12delta NII), 250 uL CaCl$_2$ (2.5M), and 50 uL spermidine (Sigma) (0.1M free base). The gold/DNA mixture is then incubated on ice for 10 minutes and centrifuged. Two ETOH (100%) washes were performed, and the gold/DNA was suspended in 72 uL ETOH (100%). The gold suspension (5.4 ul) was applied to each macrocarrier (Bio-Rad). The macrocarriers were then placed in a dessicator for at least 1 minute.

Bombardments were carried out using the DuPont PDS 1000He Biolistic gun. Rupture disks (900 psi) were used, and helium pressure and vacuum levels were 1100 psi and 27" Hg, respectively. Two days later, leaves were cut into 1 cm$^2$ pieces and places on selective regeneration medium containing spectinomycin (500 mg/L). Leaf segments from the first round regenerates were taken and placed on the same medium. Leaf segments were then taken from the second round regenerants and places on two parallel selection plates. One regeneration medium contained only 500 mg/L of spectinomycin, and the other regeneration medium contained both 500 mg/L of spectinomycin and 500 mg/L of streptomycin. Leaf segments that remained green and showed signs of callus formation or regeneration on the dual selection media were selected and placed in a regeneration medium that contained only spectinomycin for a third round of regeneration. Regenerants were transferred to Magenta boxes (Sigma, St. Louis, Mo.) until sufficient roots were grown to warrant transplantation to a greenhouse.

E. Selectable Resistance Marker for Transformations

The present invention, in addition, includes the use of the cyanobacterial pds and ahas genes as a selectable marker for transformations. To test the ability of pds and ahas genes as selectable markers, aadA, a known marker for streptomycin and spectinomycin was used as a control. Upon transformation, a plant transformed with pds or ahas and aadA should show resistance to streptomycin, spectinomycin as well as the imidazolinones or 4'-fluoro-6-[(alpha,alpha,alpha,-trifluoro-m-tolyl)oxy]-picolinamide. In this instance, aadA, a known marker for streptomycin and spectinomycin, was used as a control. Thus, a plant grown with pds or ahas and aadA should show resistance to streptomycin, spectinomycin and imidazolinones or 4'-fluoro-6-[(alpha,alpha,alpha,-trifluoro-m-tolyl)oxy]-picolinamide.

To test for cyanobacterial pds and ahas's ability as selectable markers, leaf explants were transferred to medium containing both spectinomycin and streptomycin following two rounds of regeneration under spectinomycin selection. The numbers of spectinomycin/streptomycin resistant lines for each construct can be seen on Table 3.

TABLE 3

In vitro selection of plastid transformants.

| DNA Construct | # of Bombardments | # of Discrete spectinomycin-resistant Lines | # of spectinomycin + streptomycin resistant lines |
|---|---|---|---|
| p12AN I | 35 | 6 | 3 |
| p12AN II | 35 | 5 | 3 |
| p116 | 90 | 12 | 1 |

Figure 8A:
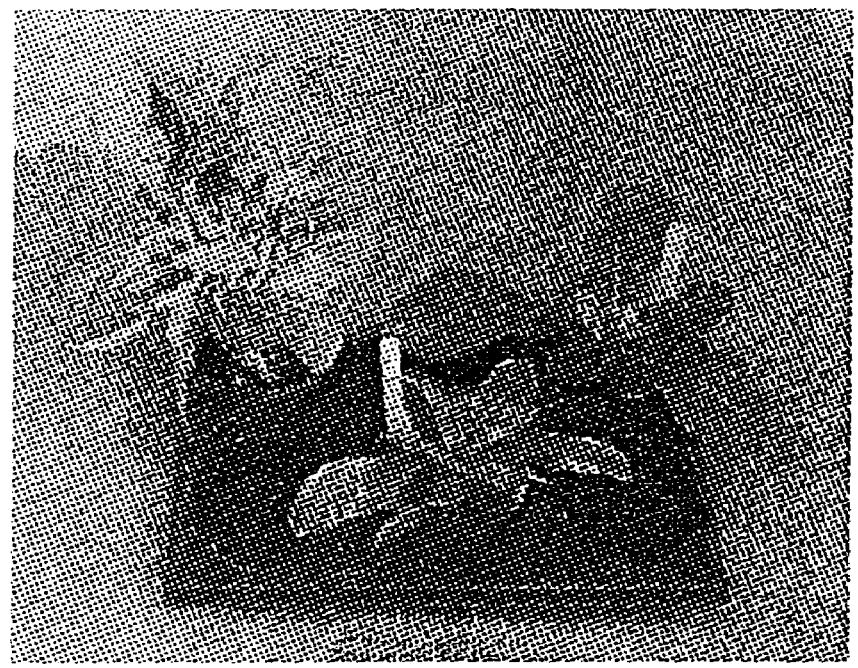
Figure 8B:
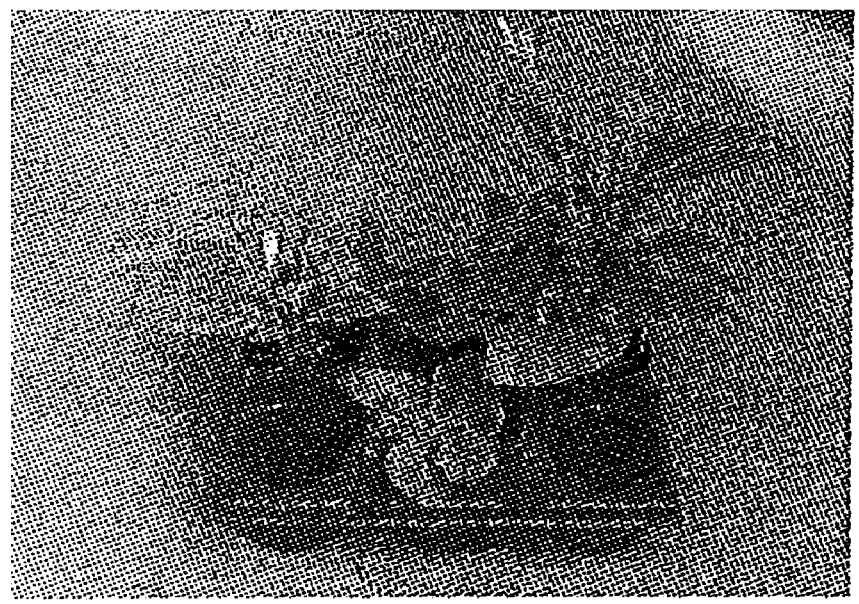

Observations and photos (FIG. 8) of the PURSUIT® imazethapyr spray test were taken 5 weeks after the test was conducted. Wild type (W-38), p 111, and p 112 lines showed wide-spread leaf necrosis and stunting of growth when sprayed at an 18 g/ha concentration, and even more extreme effects were seen at 35 g/ha. p116 line. G-981208-1.1, showed no visible leaf damage at 18 or 35 g/ha. Growth was uninhibited at 18 g/ha, although slight stunting could be observed at 35 g/ha. PURSUIT® imazethapyr appeared to act as a strong growth regulator on the p116 line, resulting in prolific shooting and morphological abnormalities in new shoots. Leaves assumed a thin, spiny form.

Figure 9B:
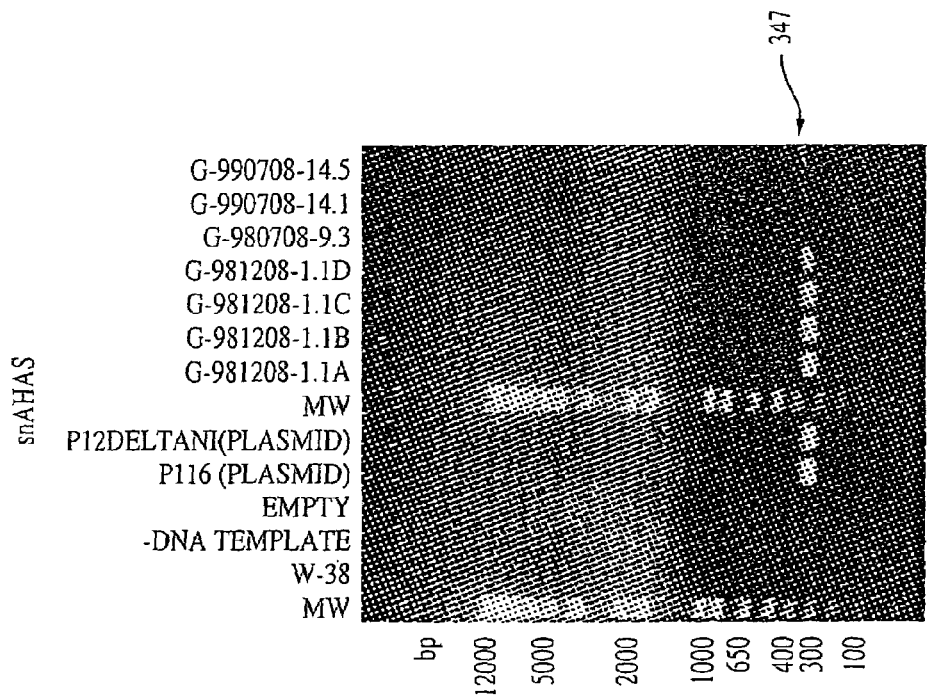
Figure 9A:
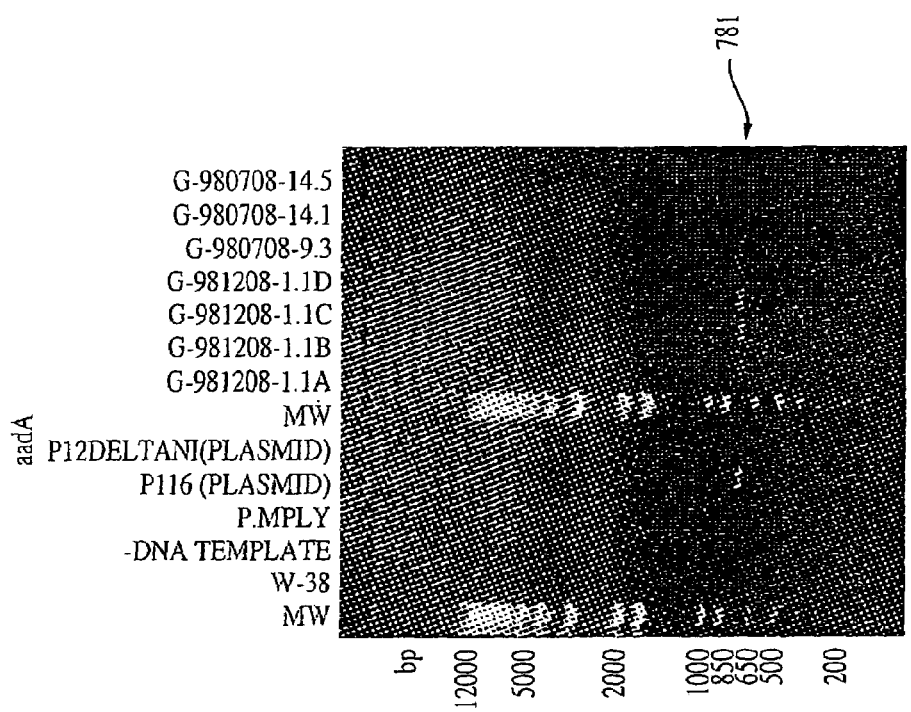

PCR amplification confirmed the integration of the *Synechocystis* AHAS gene into transplastomic line G-981208-1.1 (a–d)(FIGS. 9A and 9B). Clone a was sprayed at 35 g/ha PURSUIT® imazethapyr, clones b and c were sprayed at 18 g/ha, and clone d was not sprayed. The properly sized bands could be seen for the AHAS fragment.

Therefore, the ahas gene successfully integrated into the plastome and provided herbicide resistance. Because of this, cyanobacterial pds and ahas mutants can be used as a control selectable markers to test other types of transformations. The herbicide resistant pds and ahas genes can be coupled with selection on 4'-fluoro-6-[(alpha,alpha,alpha,-trifluoro-m-tolyl)oxy]-picolinamide or other known PDS inhibitors, and imidazolinones and other AHAS inhibiting compounds such as PURSUIT® imazethapyr for an efficient selection system for transformation. Selections can be applied to either nuclear or plastid transformation, depending on the construction of the genes.

Figure 10A:
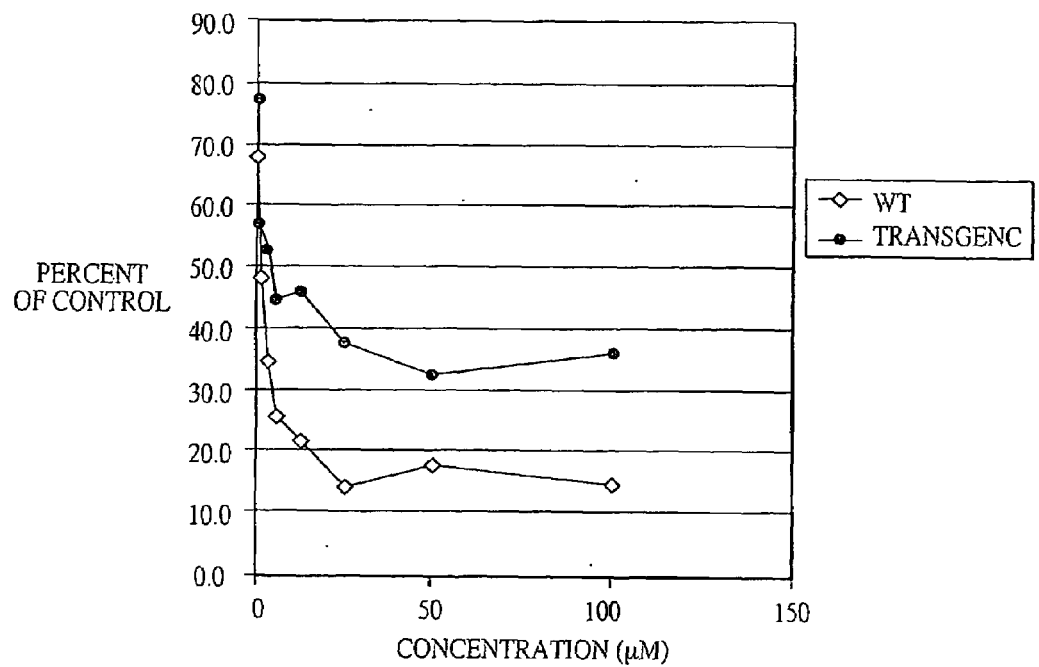
Figure 10B:
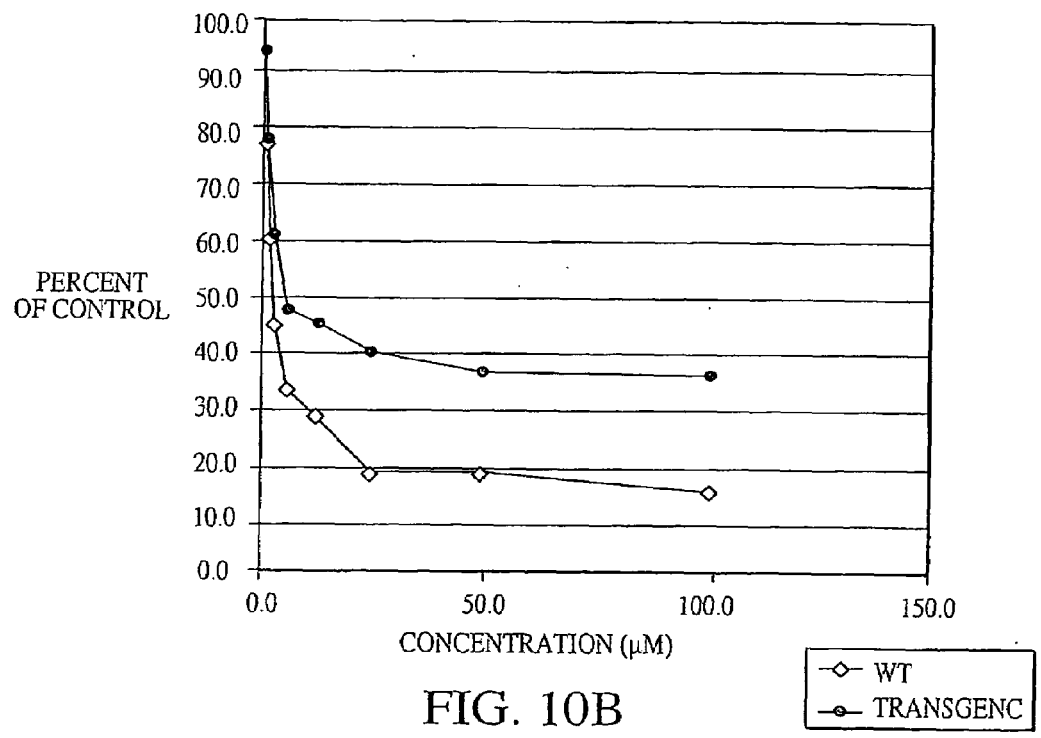

The pACBC222 line, G-981208-1.1, tobacco cultivar, Wisconsin-38 transformed with the pACBC22 (or p116 I) construct (FIG. 10) sprayed with 18 g/ba PURSUIT® imazethapyr showed about a 20% increase in AHAS enzyme resistance in the presence of PURSUIT® imazethapyr and sulfanylcarboxamides when compared with AHAS enzyme from unsprayed wild type tobacco. Interestingly enough, it appears that the snAHAS enzyme displays a level of cross resistance to both PURSUIT® imazethapyr and sulfanylcarboxamides, although they are both quite dissimilar structurally.

F. Cells, Tissue, Plants Derived from Chloroplast-Mediated Transformations

A further object of this invention provides for cells, tissue, plants, pollen derived from said transformation of the mutant *Synechocystis* pds gene and the ahas genes into untransformed plant cells, using. Alternatively, mutant forms of pds genes with mutation(s) at position(s) similar to the *Synechocystis* gene can be obtained for any given crop species, and used further for genetic transformation. *Synechocystis* mutant pds gene(s) resistant to 4'-fluoro-6-[(alpha,alpha,alpha,-trifluoro-m-tolyl)oxy]-picolinamide and the mutant AHAS gene comprising the ahas small subunit and the ahas large subunit identified in these processes can be, respectively, introduced directly into crops for engineering 4'fluoro-6-[(alpha,alpha,alpha,-trifluoro-m-tolyl)oxy]-picolinamide resistance via chloroplast-mediated transformation and imidazolinone resistance. The genes can also be used for generating resistance to other pds or AHAS inhibiting herbicides.

While the preferred embodiments of the invention has been illustrated and described, it will be appreciated that various changes can be made therein without departing from the spirit and scope of the invention.

REFERENCES

Patents

WO 9,628,014 Hirschberg et al 1996
WO 9,806,862 Calgene 1997
WO 9,820,144 Zeneca 1998
JP 6,343,473 Kirin Brewery 1994
U.S. Pat. No. 5,378,824 Dupont 1995
U.S. Pat. No. 5,661,017 Dunahay et al 1995

Other References

Babczinski, P., Sandmann, G., Schmidt, R., Shiokawa, Kozo, Yasui, Katzucsmi, Pestic. Biochem. Physiol., 1995, 52, 1, p33–44

Boger, P. Sandmann, G., Pesticide Outlook, 1998, 9, 6, p. 29–35

Chamowitz, D. Sandmann, G. Hirschberg, J., J. Biol. Chem., 1993, 268, 23, p. 17348–53

Chamovitz, D., Pecker, I., Hirschberg, J., Plant Molecular Biology, 16, pp. 967–974 (1991)

Clarke, I. E. Sandmann, G. Brawley, P. M. Boeger, P., Pestic. Biochem. Physiol., 1985, 23, 3, p. 335–340

Duggleby et al., Gene, 1997, 190, p. 245

Dzelzkalns & Bogorad, 1998, *The EMBO Journal*, 7, p. 333–338

Freiberg, D. Seijffers, J., Z Naturforsch, 1990, C, 45, 5, P. 538–543

Kowalczyl-Schroder, S. Sandmann, G., Pestic. Biochem. Physiol., 1992, 42, 1, p. 7–12

Hattori et al, Mol. & Gen. Genet., 1995, 246, p. 419–425

Linden, H., Sandmann, G., Chamovitz, D., Hirschberg, J., Booger, P. Pesticide Biochemistry and Physiology, 36, pp. 46–51 (1990)

Martinez-Ferez, I., Vioque, A., Plant Molecular Biology, 18, pp. 981–983, (1992)

Mifflin, B. J., Arch. Biochm. Biophys., 1971, 146, p. 542–550

Powell, H. A. Kerley, N. W. Powell, P., Br. Phycol. J., 1990, 25 1, p. 93

Sandmann, G. Schmidt A. Linden, H. Boger, P., Weed Science, 39, pp. 474–479 (1991)

Sandmann, G. Schneider, C. Boger, P., Z Naturforsch 1996, 51, 7–8, p. 534–538

Sandmann, G. Fraser, P. D., Z Naturforsch 1993, C,48, 3–4, p. 307–311

Sandmann, G. Schneider, C. Boger, P., Z Naturforsch 1996, 51, 7–8, p. 534–538

Sandmann, G. Fraser, P. D. Linden, H., Res. Photosynth. Proc. Int. Congr., 1992, 3, p. 51–4

Sandmann, G. Kowalczyl-Schroder, S. Taylor, H. M. Boeger, P., Pestic. Biochem. Physiol., 1992, 42, 1, p. 1–6

Sandmann, G., Target Assays Mod. Herbic. Relat. Phytotoxic Compd., 1993, p. 15–20

Sandmann, G., Chamovitz, D., Hirchberg, J., The Journal of Biological Chemistry, Vol. 268, No. 23, pp. 17348–17353 (1993)

Singh B K, Stidham M A, Shaner D L, Anal. Biochem., 1998, 171:173–179

Singh B K, Stidham M A, Shaner D L, J. Chromatography, 1998, 444, 251

Weinstock et al., J. Bacteriol., 1992, 174, p. 5560–5566

Williams et al., 1998, Methods in Enzymology, 167, p. 766–778

Windhoevel, U. Geiges, B. Sandman, G. Boeger, P., Pestic. Biochem. Physiol., 1994, 49, 1, p. 63–71

Windhoevel, U. Sandman, G. Boeger, P. Pestic, Biochem. Physiol., 1997, 57, 1, p. 68–78

Windhoevel, U., Geiges, B. Sandman, G. Boeger, P., Plant Physiol., 1994, 104, 1, p. 6371 Methods in Enzymology, 167, 703–712

What is claimed is:

1. An isolated and purified polynucleotide, encoding an acetohydroxyacid synthase (AHAS) large subunit gene, wherein the polynucleotide comprises the sequence of SEQ ID NO:6, and wherein the polynucleotide confers resistance to an herbicide selected from the group consisting of an imidazolinone, a sulfonylurea, and a sulfanylcarboxamide.

2. The isolated and purified polynucleotide according to claim 1, wherein the polynucleotide is isolated and purified from the cyanobacterium *Synechocystis* PCC 6803.

3. A replicable expression vector comprising the polynucleotide of claim 1.

4. A nuclear genome comprising the replicable expression vector of claim 3.

5. A plastome comprising the replicable expression vector of claim 3.

6. A transgenic plant produced from the transformation of a plant with the replicable expression vector of claim 3.

7. Progeny derived from the transgenic plant according to claim 6.

8. The transgenic plant according to claim 6, wherein said transgenic plant exhibits increased resistance to an herbicide selected from the group consisting of an imidazolinone, a sulfonylurea, and a sulfanylcarboxamide.

9. The replicable expression vector according to claim 3, wherein said replicable expression vector is a construct for nuclear genome transformation comprising an *Arabidopsis* AHAS large subunit promoter and transit sequence, the *Synechocystis* AHAS large subunit coding region, and an *Arabidopsis* AHAS large subunit termination sequence.

10. An isolated and purified polynucleotide encoding an acetohydroxyacid synthase (AHAS) small subunit gene, wherein the polynucleotide comprises the sequence of SEQ ID NO:17, and wherein the polynucleotide confers resistance to an herbicide selected from the group consisting of an imidazolinone, a sulfonylurea, and a sulfanylcarboxamide.

11. The isolated and purified polynucleotide according to claim 10, wherein the polynucleotide is isolated and purified from the cyanobacterium *Synechocystis* PCC 6803.

12. A replicable expression vector comprising the polynucleotide of claim 10.

13. A nuclear genome comprising the replicable expression vector of claim 12.

14. A plastome comprising the replicable expression vector of claim 12.

15. A transgenic plant produced from transformation of a plant with the replicable expression vector according to claim 12.

16. Progeny derived from the transgenic plant according to claim 15.

17. The transgenic plant according to claim 15, wherein said transgenic plant exhibits resistance to an herbicide selected from the group consisting of an imidazolinone, a sulfonylurea, and a sulfanylcarboxamide.

18. The replicable expression vector according to claim 12, wherein said replicable expression vector is a construct for nuclear genome transformation comprising an *Arabidopsis* AHAS large subunit promoter and transit sequence, the *Synechocystis* AHAS small subunit coding region, and an *Arabidopsis* AHAS large subunit termination sequence.

19. A method of producing a transgenic plant having increased resistance to an herbicide as compared to an untransformed wild type plant, comprising
   a. transforming a plant cell with a replicable expression vector comprising a polynucleotide sequence selected from a group consisting of SEQ ID NO:6 and SEQ ID NO:17; and
   b. generating from the plant cell a transgenic plant that expresses the polynucleotide sequence.

20. The method of claim 19, wherein the polynucleotide sequence is SEQ ID NO:6.

21. The method of claim 19, wherein the polynucleotide sequence is SEQ ID NO:17.

22. The method of claim 19, wherein the replicable expression vector is a nuclear transformation vector.

23. The method of claim 19, wherein the replicable expression vector is a plastid transformation vector.

* * * * *